United States Patent [19]
Staunton et al.

[11] Patent Number: 5,948,891
[45] Date of Patent: Sep. 7, 1999

[54] CYTOPLASMIC MODULATORS OF INTEGRIN BINDING

[75] Inventors: Donald E. Staunton, Kirkland; Edith A. Salot Harris, Seattle, both of Wash.

[73] Assignee: ICOS Corporation, Bothell, Wash.

[21] Appl. No.: 08/779,113

[22] Filed: Jan. 6, 1997

Related U.S. Application Data

[63] Continuation-in-part of application No. 08/583,562, Jan. 5, 1996.

[51] Int. Cl.$^6$ .................................................. A61K 38/17
[52] U.S. Cl. ........................ 530/353; 530/350; 536/23.5
[58] Field of Search .................................. 530/350, 353; 536/235

[56] References Cited

U.S. PATENT DOCUMENTS

5,506,126  4/1996  Seed et al. .

OTHER PUBLICATIONS

Altin et al., "A One–Step Procedure for Biotinylation and Chemical Cross–Linking of Lymphocyte Surface and Intracellular Membrane–Associated Molecules," *Anal. Biochem.* 224:382–389 (1995).
Arnaout, Amin M., "Structure and Function of the Leukocyte Adhesion Molecules CD11/CD18," *Blood* 75(5):1037–1050 (1990).
Baron et al. "The Pathogenesis of Adoptive Murine Autoimmune Diabetes Requires an Interaction between α4–Integrins and Vascular Cell Adhesion Molecule–1," *J. Clin. Invest.* 93:1700–1708 (1994).
Baron et al. "Surface Expression of α4 Integrin by CD4 T Cells Is Required for Their Entry into Brain Parenchyma," *J. Exp. Med.* 177:57–68 (1993).
Burkly et al., "Protection Against Adoptive Transfer of Autoimmune Diabetes Mediated Through Very Late Antigen–4 Integrin," *Diabetes* 43:529–534 (1994).
Clark and Brugge, "Integrins and Signal Transduction Pathways" The Road Taken, *Science* 268:233–239 (1995).
Cunningham et al., "Actin–Binding Protein Requirement for Cortical Stability and Efficient Locomotion," *Science* 255:325–327 (1992).
Durfee et al., "The Retinoblastoma Protein Associates with the Protein Phosphatase Type 1 Catalytic Subunit," *Genes & Developement* 7:555–569 ((1993).
Ezzell et al., "Localization of the Domain of Actin–binding Protein That Binds to Membrane Glycoprotein Ib and Actin in Human Platelets," *J. Biol. Chem.* 263(26):13302–13309 (1988).
Ferguson et al., "Antigen–Independent Processes in Antigen–Specific Immunity," *J. Immunol.* 150(4):1172–1182 (1993).
Gorlin et al., "Human Endothelial Actin–binding Protein (ABP–280, Nonmuscle Filamin): A Molecular Leaf Spring," *J. Cell Biol.* 111:1089–1105 (1990).

Gumbiner et al., "Proteins Associated with the Cytoplasmic Surface of Adhesion Molecules," *Neuron* 11:551–564 (1993).
Hemler et al., "Structure of the Integrin VLA–4 and its Cell–Cell and Cell–Matrix Adhesion Functions," *Immunol Rev.* 114:45–60 (1990).
Jutila, Mark A., "Function and Regulation of Leukocyte Homing Receptors," *J. Leukocyte Biol.* 55:133–140 (1994).
Kilshaw et al. "A New Surface Antigen on Intraepithelial Lymphocytes in the Intestine," *Eur. J. Immunol.* 20:2201–2207 (1990).
Kishimoto et al., "Cloning of the β Subunit of the Leukocyte Adhesion Proteins: Homology to an Extracellular Matrix Receptor Defines a Novel Supergene Family," *Cell* 48:681–690 (1987).
LaFlamme et al., "Regulation of Fibronectin Receptor Distribution," *J. Cell Biol.* 117(2):437–447 (1992).
Lazarovits et al., "Differential Expression in Rheumatoid Synovium and Synovial Fluid of α4β7 Integrin," *J. Immunol.* 151(11):6482–6489 (1993).
Leedman et al., "Cloning from the Thyroid of a Protein Related to Actin Binding Protein that is Recognized by Graves Disease Immunoglobulins," *Proc. Natl. Acad. Sci.* 90:5994–5998 (1993).
Lobb and Hemler, "The Pathophysiologic Role of α4 Integrins In Vivo," *J. Clin. Invest.* 94:1722–1728 (1994).
McEver, Rodger P., "Leukocyte–Endothelial Cell Interactions," *Curr. Opin. Cell. Biol.* 4:840–849 (1992).
Milne and Piper, "The Role of the VLA–4 Integrin in a Model of Airway Inflammation in the Guinea–Pig," *Br. J. Pharmacol* 112:82P (Abstr) (1994).
Miyamoto et al., "Synergistic Roles for Receptor Occupancy and Aggregation in Integrin Transmembrane Function," *Science* 267:883–835 (1995).
Mulligan et al., "Role of $α_1$, $β_2$ Integrins and ICAM–1 in Lung Injury after Deposition of IgG and IgA Immune Complexes," *J. Immunol.* 150(6):2407–2417 (1993a).
Mulligan et al., "Requirements for Leukocyte Adhesion Molecules in Nephrotoxic Nephritis," *J. Clin. Invest.* 91:577–587 (1993b).

(List continued on next page.)

*Primary Examiner*—Christina Y. Chan
*Assistant Examiner*—Patrick J. Nolan
*Attorney, Agent, or Firm*—Marshall, O'Toole, Gerstein, Murray & Borun

[57] ABSTRACT

The present invention relates to purified and isolated polynucleotides encoding a polypeptide which specifically bind to a cytoplasmic portion of an integrin. Specifically, the invention provides a FLP-1-encoding polynucleotide and the polypeptide product of the gene. Expression vectors comprising the polynucleotide, antibodies which recognize the polypeptide, hybridomas which secrete the antibodies, and method to identify modulators of interaction of the polypeptide with $β_7$ subunits sequences are also provided.

2 Claims, No Drawings

OTHER PUBLICATIONS

Nakajima et al., "Role of Vascular Cell Adhesion Molecule 1/Very Late Activation Antigen 4 and Intercellular Adhesion Molecule 1/Lymphocyte Function–associated Antigen 1 Interactions in Antigen–induced Eosinophil and T Cell Recruitment into the Tissue," *J. Exp. Med.* 179:1145–1154 (1994).

Paul et al., "The Efficacy of LFA–1 and VLA–4 Antibody Treatment in Rat Vascularized Cardiac Allograft Rejection," *Transplantation*, 55(5):1196–1199 (1993).

Pavalko and Otey, "Role of Adhesion Molecule Cytoplasmic Domains in Mediating Interactions with the Cytoskeleton," *Proc. Soc. Exp. Biol. Med.*, 205:282–293, 1994.

Podolsky et al., "Attenuation of Colitis in the Cotton–top Tamarin by Anti–$\alpha$4 integrin Monoclonal Antibody," *J. Clin. Invest.* 92:372–380 (1993).

Pretolani et al., "Antibody to Very Late Activation Antigen 4 Prevents Antigen–induced Bronchial Hyperactivity and Cellular Infiltration in the Guinea Pig Airways," *J. Exp. Med.* 180:795–805 (1994).

Schweighoffer et al., "Selective Expression of Integrin $\alpha 4\beta 7$ on a Subset of Human CD4$^+$Memory T Cells with hallmarks of Gut–Trophism," *J. Immunol.* 151(2):717–729 (1993).

Sharma et al., "Direct Interaction of Filamin (ABP–280) with the $\beta$2–Integrin Subunit CD18," *J. Immunol.* 154:3461–3470 (1995).

Springer et al., "Traffic Signals for Lymphocyte Recirculation and Leukocyte Emigration: The Multistep Paradigm," *Cell* 76:301–314 (1994).

Van der Vireen et al., "A Novel Leukointegrin, $\alpha$d$\beta$2, Binds Preferentially to ICAM–3," *Immunity* 3:683–690 (1995).

Weg et al., "A Monoclonal Antibody Recognizing Very Late Activation Antigen–4 Inhibits Eosinophil Accumulation In Vivo," *J. Exp. Med.* 177:561–566 (1993).

Winn and Harlan, "CD18–Independent Neutrophil and Mononuclear Leukocyte Emigration into the Peritoneum of Rabbits," *J. Clin. Invest.* 92:1168–1173 (1993).

Yang et al., "Inhibition of Insulitis and Prevention of Diabetes in Nonobese Diabetic Mice by Blocking L–selectin and Very Late Antigen 4 Adhesion Receptors," *Proc. Natl. Acad. Sci. USA* 90:10494–10498 (1993).

Yednock et al., "Precention of Experimental Autoimmune Encephalomyelitis by Antibodies Against $\alpha 4\beta 1$ Integrin," *Nature* 356:63–66 (1992).

CYTOPLASMIC MODULATORS OF INTEGRIN BINDING

This application is a continuation-in-part of co-pending U.S. patent application Ser. No. 08/583,562 which was filed on Jan. 5, 1996, pending.

FIELD OF THE INVENTION

The present invention relates generally to filamine-like integrin binding proteins and more particularly to the cloning and expression of a novel filamine-like protein, FLP-1.

BACKGROUND

A significant characteristic of the immune and inflammatory responses is the movement of leukocytes from the bloodstream into specific tissues in response to various physiological signals. For example, certain subsets of lymphocytes "home" to various secondary lymphoid tissues such as lymph nodes or Peyer's patches, and eventually return to circulation. Other leukocytes such as granulocytes and monocytes, however, do not return to circulation after transmigration from the bloodstream. Movement of leukocytes from circulation is effected by a series of receptor/counter-receptor interactions which are coordinated by various specific membrane adhesion molecules.

Extravasation of leukocytes from the bloodstream [for review, see McEver, *Curr. Opin. Cell Biol.* 4:840–849 (1992)] is initially effected by a family of membrane glycoproteins termed selections which are either expressed constitutively or induced in response to specific cytokines. Binding of selections to their counterpart ligand brings leukocytes into close, but not static, contact with vascular endothelial cells. The "tethered" leukocyte then begins a "rolling" process along the endothelium which continues until additional molecular interactions firmly stabilize a specific cell/cell interaction. One of the molecular binding activities which results in the stable interaction is effected by a second family of surface glycoproteins called integrins which possess a higher binding affinity for their respective ligands than selectins.

The integrins are heterodimeric surface molecules comprised of an $\alpha$ and a $\beta$ subunit in non-covalent association. All integrins are transmembrane proteins with counter-receptor binding activity localized in the extracellular domain. Integrins also possess relatively short cytoplasmic regions which participate in transmembrane signaling events. Integrins are capable of interacting with other cell-bound counter-receptors and components of the extracellular matrix, as well as soluble factors. Binding of extracellular ligands leads to crosslinking and localized clustering of integrins [Miyamoto, et al., *Science* 267:833, 1995] and formation of focal adhesions wherein the clustered integrin cytoplasmic domains associate with cytoskeletal components including, for example, actin filaments [Pavalko and Otey, *Proc. Soc. Exp. Biol. Med.* 205:32767, 1994, and Gumbiner, Neuron 11:551, 1993]. While most investigations into integrin physiological activity have focused on identifying specific counter-receptors using immunological methodologies as discussed infra, less is known about the specific interactions of integrins with cytoplasmic components. Mutation studies, however, have indicated that the cytoplasmic sequences are required for integrin association with focal contacts and integrin dependent cell adhesion [LaFlamme, et al., *J. Cell. Biol.* 117:437 (1992)]. Other data discussed infra support this observation.

While numerous integrins have been identified, certain subsets are unique to leukocytes, with each member of the subset having characteristic cell-specific expression and counter-receptor binding properties. Of leukocyte-specific integrins, at least three $\beta_2$ integrins are known, each comprised of a unique $\alpha$ subunit in association with a $\beta_2$ subunit (designated CD18) [Kishimoto, et al., *Cell* 48:681–690 (1987)]. For a recent review of the state of the art with regard to $\beta_2$ integrins, see Springer, Cell 76:301–314 (1994). CD11a/CD18, also known as $\alpha_L\beta_2$ or LFA-1, is expressed on all leukocytes and has been shown to bind to ICAM-1, ICAM-2, and ICAM-3. CD11b/CD18, also know as $\alpha_M\beta_2$ or Mac-1, is expressed on polymorphonuclear neutrophils, monocytes and eosinophils and has been shown to bind to ICAM-1, complement factor iC3b, factor X, and fibrinogen. CD11c/CD18, also known as $\alpha_X\beta_2$ or p150,95, is expressed on monocytes, polymorphonuclear neutrophils and eosinophils and has been shown to bind to complement factor iC3b and fibrinogen. In addition, a fourth human $\beta_2$ integrin, designated $\alpha_d\beta_2$, has recently been identified [Van der Vieren, et al., *Immunity* 3:683–690 (1995)]. Recently, it has been demonstrated that the actin-binding protein, filamin, directly binds to a cytoplasmic portion of $\beta_2$ subunits [Sharma, et al., *J. Immunol.* 154:3461–3470 (1995)] which suggests a role for one or more of the $\beta_2$ integrins in formation of focal contacts and cell motility in general [see review in Arnaout, *Blood* 75:1037 (1990)].

A second subset of leukocyte specific integrins may be referred to as the $\alpha_4$ integrins in view of the fact that both members of the family are comprised of a common $\alpha_4$ subunit in association with either a , $\beta_1$ or $\beta_7$ subunit. For a recent review, see Springer, supra. VLA-4, also referred to as $\alpha_4\beta_1$ or CD49d/CD29, is expressed on most peripheral blood leukocytes except neutrophils and specifically binds VCAM-1 and fibronectin. LPAM-1, also known as $\alpha_4\beta_7$, is expressed on all peripheral blood leukocytes and has been shown to bind MadCAM-1, fibronectin and VCAM-1. Expression of either of the $\alpha_4$ integrins has also been demonstrated in a wide range of leukocyte cell types in lymphoid organs and in various tissues Hemler et al, *Immunol. Rev.* 114:45–60, 1990; Kilshaw et al., *Eur. J. Immunol* 20:2201–2207, 1990; Schweighoffer et al., J. Immunol 151:717–729, 1993; and Lazarovits and Karsh, *J. Immunol.* 151:6482–6489, 1993). Consistent with the observed participation of $\beta_2$ integrins in formation of focal contacts, presumably through filamin binding, it has previously been shown that cytoplasmic portions of $\beta_1$ integrins directly bind $\beta$-actinin in vitro. While this interaction has not been demonstrated in vivo, it suggests physiological involvement of $\beta_1$ integrins in cell mobility and/or maintenance of cell morphology [see review in Clark and Brugge, *Science* 268:233–238 (1995)].

A number of in vitro and in vivo studies utilizing anti-$\alpha_4$ monoclonal antibodies have indicated a role for the $\alpha_4$ integrins in various pathophysiological conditions [see review, Lobb and Hemler, *J. Clin. Invest.* 94:1722–1728 (1994)]. For example, several investigations have provided evidence that $\alpha_4$ integrins are involved in leukocyte emigration from peripheral blood into regions of inflammation (Weg, et al., *J. Exp. Med.* 177:561–566, 1992; Winn and Harlan, *J. Clin. Invest.* 92:1168–1173, 1993). These observations suggest that anti-$\alpha_4$ antibodies may be capable of ameliorating integrin-associated disease states, and this therapeutic potential has been demonstrated in several animal disease state models. For example, bolus injection of antibodies to $\alpha_4$ integrins delayed the onset of paralysis in rat and murine experimental allergic encephalomyelitis (Yednock, et al., *Nature* 356:63–66, 1992; Baron, et al., *J. Exp. Med.* 177:57–68, 1993). Prophylactic administration of anti-$\alpha_4$ antibodies reduced ear swelling in murine contact hypersensitivity models (Ferguson, et al., *J. Immunol.* 150:1172–1182, 1993; Nakajima, et al., *J. Exp. Med.* 179:1145–1154, 1994). Further, anti-$\alpha_4$ antibodies were shown to reduce infiltration of pancreatic islets and delay the onset of diabetes in non-obese diabetic mice which are prone to spontaneous development of type I diabetes (Yang, et aL, *Proc. Natl. Acad. Sci.* (*USA*) 90:10494–10498. 1993; Burkly, et al., *Diabetes* 43:529–534, 1994; Baron, et al., *J. Clin. Invest.* 93:1700–1708, 1994). Still other in vivo studies using anti-$\alpha_4$ antibodies suggest a role for $\alpha_4$ integrins in allergic lung inflammation (Pretolani, et al., *J. Exp. Med.* 180:795–805 (1994); Milne and Piper, *Br. J. Pharmacol.* 112:82Pa(Abstr), 1994); inflammatory bowel disease (Podolsky, et al.,*J. Clin. Invest.* 92:372–380, 1993); cardiac allograft rejection (Paul, et al, *Transplantation* 55:1196–1199, 1993); acute nephrotoxic nephritis (Mulligan, et al., *J. Clin. Invest.* 91:577–587, 1993); and immune complex mediated lung injury (Mulligan, et al., *J. Immunol.* 159:2407–2417, 1993).

Thus there exists a need in the art to identify molecules which bind to and/or modulate the binding and/or signaling activities of the integrins and to develop methods by which these molecules can be identified. The methods, and the molecules thereby identified, will provide practical means for therapeutic intervention in u integrin-mediated immune and inflammatory responses.

BRIEF DESCRIPTION OF THE INVENTION

In one aspect, the present invention provides novel purified and isolated polynucleotides (e.g., DNA and RNA transcripts, both sense and antisense stands) encoding a filamin-like $\beta_7$ integrin binding protein designated FLP-1, or variants thereof (i.e., deletion, addition or substitution analogs) which possess binding and/or immunological properties inherent to FLP-1. Preferred DNA molecules of the invention include cDNA, genomic DNA and wholly or partially chemically synthesized DNA molecules. Presently preferred polynucleotides include the DNA as set forth in SEQ ID NO: 1, encoding the polypeptide according to SEQ ID NO:2. Alternatively, a preferred polynucleotide encodes a polypeptide according to SEQ ID NO: 2 except that the amino acid at position 146 is a proline rather than a leucine, the amino acid at position 442 is a proline rather than an alanine and the amino acid at position 548 is a valine rather than a methionine. Such a polynucleotide would hybridize to the DNA set out in SEQ ID NO: 1.

Preferred polynucleotides of the invention comprise the cDNA set out in SEQ ID NO: 1 and DNAs which hybridize to the non-coding strands thereof under stringent conditions or which would hybridize but for the redundancy of the genetic code. Exemplary stringent hybridization conditions are as follows: hybridization at 42° C. in 5×SSPE and a final wash at 65° C. in 0.2×SSC. It is understood by those of skill in the art that variation in these conditions occurs based on the length and GC nucleotide content of the sequences to be hybridized. Formulas standard in the art are appropriate for determining exact hybridization conditions. See Sambrook, et al., Eds. 9.47–9.51 in *Molecular Cloning,* Cold Spring Harbor Laboratory Press, Cold Spring Harbor, N.Y. (1989).

Also provided are recombinant plasmid and viral expression constructs which include FLP-1 encoding sequences, wherein the FLP-1 encoding sequence is operatively linked to a homologous or heterologous transcriptional regulatory element or elements.

As another aspect of the invention, prokaryotic or eukaryotic host cells, transformed or transfected with polynucleotide sequences of the invention, are provided which express FLP-1 polypeptides or variants thereof. Host cells of the invention are particularly useful for large scale production of FLP-1 polypeptides which can be isolated from the host cell itself or the medium in which the host cell is grown.

Also provided by the present invention are purified and isolated FLP-1 polypeptides, including fragments and variants thereof. Novel FLP-1 polypeptides of the invention may be isolated from natural sources, but along with FLP-1 variant polypeptides, are preferably produced by recombinant procedures involving host cells of the invention. Variant FLP-1 polypeptides, including fully glycosylated, partially glycosylated, and wholly de-glycosylated forms of the FLP-1 polypeptide may be generated, depending on the host cell selected for recombinant production and/or post-isolation processing. Additional variant FLP-1 polypeptides include water soluble and insoluble FLP-1 polypeptides and fragments thereof, analogs wherein one or more amino acids are deleted from, replaced in, or added to the preferred FLP-1 polypeptide, polypeptide analogs with equal or enhanced biological activities and/or immunological characteristics specific for FLP-1, and analogs with modified ligand binding and/or signal transducing capabilities. Fusion polypeptides are also provided wherein FLP-1 amino acid sequences are expressed contiguously with amino acid sequences derived from other polypeptides. Fusion polypeptides of the invention include those with modified biological, biochemical, and/or immunological properties in comparison to the preferred FLP-1 polypeptide.

Also contemplated by the present invention are antibodies and other peptide and non-peptide molecules which specifically bind to FLP-1. Binding molecules of this type are particularly useful for purifying FLP-1 polypeptides, identifying cell types which express FLP-1 polypeptides, and assaying for presence or absence of FLP-1 polypeptides in a fluid. Binding molecules are also useful for modulating (i.e., blocking, inhibiting, or stimulating) in vivo binding and/or signal transduction activities of FLP-1. Antibodies of the invention include monoclonal, polyclonal, and recombinant (i.e., humanized, chimeric, etc.) forms and fragments thereof.

Also contemplated by the invention are hybridomas which secrete monoclonal antibodies specifically immunoreactive with FLP-1. Likewise, cell types modified by recombinant means so as to express and/or secrete genetically engineered FLP-1 binding molecules are also comprehended.

Assays to identify FLP-1 binding molecules are also provided, including immobilized ligand binding assays, solution binding assays, scintillation proximity assays, two hybrid screening assays, immunological methodologies and the like. In addition to identifying FLP-1 binding molecules, the same or similar assays are useful for identification of molecules which modulate FLP-1 specific binding. For example, assays to identify modulators (i.e., activators or inhibitors) of FLP-1 specific binding can involve a) contacting FLP-1 or a fragment thereof, with $\beta_7$ integrin or a fragment thereof; b) measuring binding between FLP-1 or a fragment thereof, and $\beta_7$ integrin or a fragment thereof; c) measuring binding between FLP-1 or a fragment thereof, and $\beta_7$ integrin or a fragment thereof in the presence of a test compound, and d) comparing the measurement in step (b) and the measurement in step (c) wherein a decrease in binding in step (c) indicates the test compound in an inhibitor of binding, and an increase in binding in step (c) indicates the test compound is an activator of binding.

Variations on the method to identify modulators of FLP-1 binding can include scintillation proximity assays comprising the steps of immobilizing either FLP-1 or its binding partner on a solid support, wherein the solid support contains a fluorescent agent; modifying the non-immobilized binding partner to include a compound that can excite the immobilized fluorescent agent; contacting the non-immobilized binding partner with the immobilized binding partner; determining the level of light emission for the fluorescent agent; and repeating the procedure in the presence of a putative modulator of FLP-1 binding.

As still another variation of the method, a two hybrid system may be utilized to identify genes encoding potential modulators. In this system, an integrin sequence is expressed in a host cell as a fusion protein with either a DNA binding domain or transactivation domain of a modular transcription factor. A binding partner protein is also expressed as a fusion protein with the transcription factor domain not utilized in expressing the integrin fusion protein. Interaction of the two fusion proteins results in reconstitution of the holo-transcription factor and permits expression of a reporter gene with a promoter specific for the transcription factor. Use of this system in the presence or absence of library cDNA can permit identification of genes that encode proteins which modulate the degree of reporter gene expression.

Additional methods comprehended by the invention include immunological assays including radio-immuno assays, enzyme linked immunosorbent assays, sandwich assays and the like. Co-precipitation methods are also comprehended wherein an antibody immunospecific for one binding partner is utilized in a method in which the other binding partner is detectably labeled. Immunological assays may also include use of labeled antibodies specifically immunoreactive with a complex between the desired binding partners.

Numerous compounds are contemplated as being candidates for testing in methods of the invention. For example, antibody products which are immunoreactive with one binding partner and which modulate binding between the two molecules can be identified by the claimed method. Antibody products contemplated are monoclonal antibodies, and fragments thereof, humanized antibodies, and/or single chain antibodies. Other molecules which can be screened in the claimed method include peptides, small molecules and libraries composed of either of the same.

Modulators of $\beta_7$/FLP-1 and $\beta_7$/filamin interaction identified by the methods of the invention are utilized in vitro or in vivo to affect inflammatory processes involving leukocytes. In addition, modulating compounds which bind to either the $\beta_7$ integrin, filamin or FLP-1 are useful to monitor the level of its binding partner, either in a body fluid or biopsied tissue.

Those of ordinary skill in the art will readily appreciate that numerous variations of the claimed method are encompassed by the invention.

DETAILED DESCRIPTION OF THE INVENTION

The present invention is illustrated by the following examples relating to the isolation of a cDNA clone encoding FLP-1. Example 1 relates to identification of genes in a human B cell cDNA library that encode proteins which interact with $\beta_7$ integrin. Example 2 describes identification of genes in a human spleen cDNA library which encode proteins that interact with $\beta_7$ integrin. Example 3 addresses tissue specific expression of FLP-1. Example 4 describes specificity of interaction between filamin and $\beta_7$ and FLP-1 and $\beta_7$ integrin. Example 5 describes localization of $\beta_7$ sequences required for filamin or FLP-1 binding. Example 6 relates to applications for modulators of $\beta_7$/filamin or $\beta_7$/FLP-1 interactions.

EXAMPLE 1

Identification of Genes in a B Cell Library Encoding $\beta_7$ Interacting Proteins The two-hybrid system developed in yeast [Durfee, et al., Genes and Development 7:555–567 (1993)] was used to screen for proteins expressed in a human B cell cDNA library which interact with the carboxy-terminal cytoplasmic tail of the $\beta_7$ integrin. The yeast two-hybrid screen is based on in vivo reconstitution of the GAL4 transcription factor and subsequent expression of a reporter gene driven by a GAL4 promoter. Briefly, GAL4 DNA-binding and transcription-activating domains are encoded on separate plasmids as portions of fusion proteins. Expression of the fusion proteins and interaction of the expression products results in association of the two GAL4 domains and ultimate expression the ,β-galactosidase reporter gene under transcriptional control of the GAL4 promoter.

In the present investigation, a "bait" plasmid (pAS1) was constructed that contained sequences encoding the GAL4-binding domain, a trp⁻ selection requirement, a hemagglutinin (HA) epitope tag and cytoplasmic amino acid sequences of $\beta_7$ integrin. The $\beta_7$ integrin cytoplasmic domain was amplified by PCR using $\beta_7$ primers set out in SEQ ID NO:3 and 4.

NHβ₇5 CGGATCCTCGGATACCGGCTCTCGGT-GAAG (SEQ ID NO: 3)

NHβ₇3 CGGCTCCTCAGAGAGTGGGACTGTCT-GCCT (SEQ ID NO: 4)

Reaction conditions included an initial incubation at 94° C. for four minutes, followed by thirty cycles of: 94° C. for one minute, 50° C. for two minutes, and 72° C. for four minutes. The resulting product was sequenced to rule out PCR-derived errors and subcloned into vector pAS1. A yeast strain, Y190, was transformed with $\beta_7$/pAS1 by standard methods and grown in selective media (trp⁻) to mid-log phase. Cells were lysed in lysis buffer (containing 100 mM Tris, pH 6.8, 2% SDS, 10% glycerol, 5% BME and 0.1% bromo phenol blue) and the equivalent of 5–6×10⁶ cells of protein was separated on a 12% polyacrylamide gel. Proteins in the gel were transferred to a PVDF (Millipore, Bedford, Mass.) membrane by standard methods. Control lanes on the gel contained lysate from Y190 cells transformed with pAS1 vector alone (containing no $\beta_7$ integrin-encoding sequences). Western blotting was performed using antibody 12CA5, immunospecific for the HA epitope tag, (Boehringer Mannheim, Indianapolis, Ind.) and a goat anti-mouse IgG horse radish peroxidase (HRP) secondary antibody. Results, in combination with size determination using SDS-PAGE, confirmed that the fusion protein $\beta_7$ integrin cytoplasmic tail/HA/GALA DNA-binding domain was expressed at readily detectable levels.

A "target" vector was constructed with vector pACT modified to contain sequences encoding the GALA activation domain II fused to a B cell cDNA library and a leu⁻selection requirement. Lymphocyte cDNA library sequences were inserted at an XhoI site of the vector. $\beta_7$/pAS1-transformed Y190 cells were transformed by standard methods with the pACT-lymphocyte library DNA and cells grown under selective conditions (leu⁻/trp⁻/his⁻3-aminotriazole). Resulting colonies were tested for β-galactosidase (β-gal) activity by the blue/white selection method well known in the art and forty-four β-gal positive clones were obtained. Sequence analysis of the B cell cDNA-derived pACT inserts in each of the clones revealed twenty novel sequences and twenty four sequences encoding known proteins or portions of known proteins.

Five clones were of particular interest, all of which contained sequences encoding a portion of the non-muscle protein filamin, or actin-binding protein ABP280(emb/X53416), [Gorlin, et al., *J. Cell Biol.* 111:1089–1105 (1990)]. All five clones were shown to encode the carboxy-terminal portions of filamin (SEQ ID NO: 7) and each clone extended into 3' untranslated portions of the filamin gene. Clone 411 corresponded to sequences in repeat 20 (beginning at nucleotide 6763 in SEQ ID NO: 7) and clones 514, 1521, 1271 and 722 beginning in repeat 23 (each beginning at nucleotide 7513, 7552, 7579, and 7579 in SEQ ID NO: 7, respectively). There was one discrepancy between the published sequence of filamin and the sequences determined in each of the positive clones: all positive clones had an aspartate residue at position 2634, while the published sequence of filamin had a histidine at that position. Of these clones, 1271, 514 and 411 were selected for subsequent analysis, and the nucleotide and amino acids sequences of 1271 are set out in SEQ ID NOs: 5 and 6, respectively.

EXAMPLE 2

Identification of Genes in a Human Spleen Library Encoding β$_7$ Interacting Proteins The two-hybrid system described in Example 1 was repeated using human spleen cDNA library sequences (Clontech, Palo Alto, Calif.) cloned into an EcoRI site of the target vector pGAD10 (Clontech).

After transformation of the β$_7$/pAS1 Y190 strain with the spleen/pGAD10 plasmid and selection as previously described, the resulting colonies were tested for β-gal activity and six positive clones were identified. Sequence analysis of the six β-gal positive clones that revealed five identical clones (from which clone S5 was selected for further analysis) along with clone S3, (the sixth positive clone and distinct from the other five) were identified.

DNA and protein alignments revealed that clones S3 and S5 encode different, but overlapping regions of the same protein, with the S3 insert beginning 5' of the S5 insert, and terminating before the 3' end of clone S5. The DNA sequences of clones S3 and S5 were compared to DNA databases using NCBI Blastn with default parameters on Oct. 16, 1995, and both clones were found to exhibit approximately 70% identity to filamin. The nucleotide and amino acid sequences of clone S3 are set out in SEQ ID NOs: 9 and 10, respectively. Sequences for clone S5 are set out in SEQ ID NOs: 11 and 12, respectively. The composite protein encoded by the overlapping clones S3 and S5 was designated FLP-1 (filamin like protein). Blastp search of protein database (NCBI Blastp) revealed that the composite protein FLP-1 has a 73% identity to fidamin. Alignment of FLP-1 to filamin shows that clones S3 and S5 represent carboxy terminal regions of FLP-1. When FLP-1 is aligned with filamin in the second hinge region between repeats 23 and 24, the putative glycoprotein binding region, the degree of identity drops to 38%, suggesting a difference in binding affinity between filamin and FLP-1 for membrane glycoproteins.

In addition, a region of clone S5 was further found to exhibit 100% identity to truncated actin-binding protein TABP (GP or GB/M62994), a protein previously shown to be a truncated, non-actin-binding filamin-like protein [Leedman, et al., *Proc.Natl.Acad.Sci.(USA)* 90:5994–5998 (1993)] having 195 amino acids and a molecular weight of approximately 21 kDa. Identity was particularly high between nucleotides 950–1515 of clone 5 which were 95–99% identical to regions of TABP. TABP lacks an actin binding domain and 22 of 24 tandem repeats found in filamin, but contains sequences homologous to the carboxy terminal repeats numbered 23 and 24 found in filamin. The TABP hinge region, between repeats 23 and 24, contains a putative glycoprotein binding site and a $Ca^{2+}$/calmodulin kinase II phosphorylation site [Leedman, supra]. TABP is encoded by a 2.3 kb MRNA and a cDNA encoding TABP was cloned from a thyroid expression library from a Graves disease patient [Leedmen, supra].

In order to obtain a more complete FLP-1 sequence, the human spleen cDNA library was screened using S3 as a probe. The S3 clone was digested with EcoRI and a 1.2 kb fragment was isolated and labeled using the Random Primed Labeling Kit (Boehringer Mannheim, Indianapolis, Ind.) according to the manufacturer's suggested protocol. Unincorporated nucleotides were removed using a Centrisep column (Princeton Separations, Adelphia, N.J.). The probe was added to filters in hybridization solution (5×SSPE, 45% formamide, 5× Denhardts, 1% SDS) and hybridized overnight at 42° C. The filters were washed at a final stringency of 0.2× SSC/0.1% SDS at 65° C.

Primary positive clones were picked, diluted and replated on Hybond N$^+$filters on LBM plates. Two duplicate filters were rehybridized with hybridization solution saved from the original hybridization described supra. Clones which were positive on both filters were picked, grown and their plasmids isolated and sequenced by standard methods.

Ten FLP-1 positive clones were detected and partial sequence data from these clones was compared to filamin and FLP-1 sequences derived from clones S3 and S5. Overlap of sequences from clones S3 and S5 with sequences from clones F3, F5 and F7 permitted determination of a more complete sequence for FLP-1, the more complete nucleotide and amino acid sequences set out in SEQ ID NOs: 1 and 2, respectively. In SEQ ID NO: 1, nucleotides 1–315 were derived from clone F5 (clone F5 was significantly longer than 315 nucleotides); nucleotides 316–738 from clone F3; nucleotides 739–816 from clone F7; nucleotides 817–1122 from clone S3 and nucleotides 1123–2574 from clone S5.

The longest clone, F5, was later sequenced in its entirety. There are five differences at the nucleotide level between SEQ ID NO: 1 and the F5 sequence. In the F5 sequence, nucleotide 437 is C rather than T changing amino acid residue 146 from leucine to proline. Nucleotide 1324 is C rather than G changing amino acid residue 442 from alanine to proline. Nucleotide position 1642 is changed G rather than A thus changing residue 548 from methionine to valine. In addition, nucleotide 2124 is C rather than T and nucleotide 2181 is A rather than T. The nucleotide differences at positions 2124 and 2181 do not alter the encoded amino residue. The sequence differences between the composite sequence of SEQ ID NO: 1 and the corresponding F5 FLP-1 sequence may arise from genetic polymorphism or the like.

EXAMPLE 3

Tissue Specific Expression of FLP-1

In order to determine size of a MRNA encoding FLP-1 in various tissues, a human immune system multiple tissue northern (Clontech) was probed with a random-primed portion of clone S3 (corresponding to nucleotides 255–777 in SEQ ID NO: 9) according to manufacturer's suggested protocol. The RNA utilized in the Northern blots included RNA from appendix, thymus, lymph node, spleen, bone marrow, fetal liver and peripheral blood leukocytes, and cell lines G361, SW480, K562, HeLa, HL60, MOLP-4, Raji and A549.

In spleen, lymph node, thymus, bone marrow, and fetal liver, mRNA of two distinct sizes hybridized to the FLP-1 probe: one just above and one just below the 9.5 Kb size marker. In appendix and peripheral blood leukocytes, only one band, just below the 9.5 Kb size marker, hybridized with the FLP-1 probe. These results suggest that the FLP-1 MRNA encodes a protein similar in size to filamin as reported in Gorlin, supra.

To determine whether filamin and FLP-1 are expressed in the same or in different cell types, Northern blots of mRNA isolated from various tissues and cell types were probed as described above. An antisense oligonucleotide filamin probe, GGTGGCCTTGGTCAGAGAGTCTACAAACAC (SEQ ID NO: 37), and an antisense oligonucleotide FLP-1 probe, GGCGCTATAGCAGGTCTCTGTAGACGACCT (SEQ ID NO: 38) were derived from hinge sequences between repeats 23 and 24 that differ in 23 out of a total of 30 nucleotides. These oligonucleotides possess approximately equivalent Tms, 81 and 82° C., respectively. The oligonucleotides were 5' labelled with $^{32}P$ and unincorporated nucleotides were removed using a G-25 Sephadex Quickspin column (BMB).

The FLP-1 probe was added to the hybridization solution (5× SSPE, 2×Denhardt's, 0.5% SDS, 100 μg/ml sheared salmon sperm DNA) and multitissue northerns (Clontech) were hybridized overnight at 42° C. Filters were washed according to the manufacturer's suggested protocol at a final stringency of 2×SSC/0. 1% SDS at 42° C.

After exposure to film, the filters were stripped according to the manufacturer's suggested protocol and exposed to flow again to ensure that the signal due to the FLP-1 probe had been completely removed. The filters were then hybridized with the filamin probe.

The FLP-1 probe detected two mRNAs, of approximately 9.5 and 8.5 kb, in several lymphoid and non-lymphoid tissues and cell lines. The filamin probe hybridized to a mRNA of approximately 8.5 kb. The levels of filamin mRNA detected in appendix, as well as epithelial (G361) and myelomonocytic (HL60) cell lines, appear to be markedly greater than that of FLP-1 and can be visualized in a 16 hour exposure. In contrast, FLP-1 mRNA expression is lower and can be detected only by exposing the film for at least seven days. Thus, FLP-1 and filamin mRNA are similar in size but appear to be differentially expressed in some tissues or cell types.

EXAMPLE 4

Specificity of Filamin/$\beta_7$ and FLP-1/$\beta_7$ Interaction

The specificity of the interactions of filamin (clones 1271 and 514) and FLP-1 with the $\beta_7$ integrin cytoplasmic tail was verified by transforming filamin clone 1271 and FLP-1 clone S5 into Y190 strains containing any one of a variety of "baits" vectors (encoding $\beta_2$, $\beta_7$ or $\alpha_L$ integrin cytoplasmic tails) using standard methods described supra. Results from this assay, shown in Table 1, indicated that filamin clone 1271 specifically binds to $\beta_7$ integrins but not to other integrins and FLP-1 clone S5 interacts with $\beta_7$ integrins.

TABLE 1

Binding Specificity of Filamin and FLP-1
SPECIFICITY OF INTERACTION

| INTEGRIN "BAIT" | FILAMIN | FLP-1 |
|---|---|---|
| $\beta_2$ | − | − |
| $\beta_7$ | + | + |
| $\alpha_L$ | − | − |

In vivo interaction between endogenous filamin and $\beta_7$ integrin was also investigated by co-precipitation of a filamin/$\alpha_4\beta_7$ complex from JY cells, which express endogenous $\alpha_4\beta_7$. Cells were initially permeabilized with 10 μg/ml lysolecithin (Sigma, St. Louis, Mo.) in PBS, pH 8.0, with 1 mM Ca$^{++}$ and 1 mM Mg$^{++}$, for five minutes. Cellular proteins were crosslinked using DTSSP (921 μM) and labeled with biotin as described in Altin, et al., *Anal. Biochem.* 224:382–389 (1995). Crosslinked proteins were solubilized using 1% Triton-X100 and integrins were immunoprecipitated using monoclonal antibodies immunospecific for $\alpha_4$ (antibody HP2/1, Immunotech, Westbrook, Me., or antibody B5G10, Upstate Biotechnology, Inc., Lake Placid, N.Y.), or $\beta_2$ (antibody 23 IIIb). A control antibody, PC21 (Sigma, St. Louis, Mo.) was also employed. Precipitated proteins were separated on a 6% SDS-PAGE gel, transferred to an Immobilon P membrane and probed with filamin antisera (Chemicon International, Inc. Temecula, Calif.).

These results demonstrate co-precipitation of naturally occurring filamin with an $\alpha_4$ integrin. Also in this assay, filamin co-precipitated with the $\beta_2$ subunit, but was not precipitated with control antibody PC21. This implies that a portion of the filamin molecule not encoded by clone 1271 interacts with a $\beta_2$ integrin.

EXAMPLE 5

Localization of FLP-1 or Filamin Binding on $\beta_7$

In order to more fully characterize the binding between FLP-1 or filamin and the cytoplasmic tail of $\beta_7$ integrin, the two-hybrid assay was employed using various deletion derivatives of either of the individual binding partners.

Several cytoplasmic domain mutants of the $\beta_7$ integrin were created using site directed mutagenesis in order to map the site(s) of interaction observed as described above. Filamin truncates (ABPD1, ABPD2 and ABPD5) and clones 1271, 514 and 411 and FLP-1 clones S5 and S3 were employed to evaluate the degree to which mutations in the $\beta_7$ cytoplasmic domain affected binding. Following standard co-transformations of Y190 as described above, binding interactions were determined by $\beta$-gal assay, as described above. The $\beta_7$ deletions utilized in these assays are set out in SEQ ID NOS: 14 to 18 and 39–41 below, and compared to the native $\beta_7$ sequence set out in SEQ ID NO: 13. In each expression construct, only the cytoplasmic portion of $\beta_7$, or a truncation thereof, was subcloned.

| | | |
|---|---|---|
| β₇ | YRLSVEIYDRREYSRFEKEQQQLNWKQDSNPLYKSAITTTINPRFQEADSPTL | (SEQ ID NO: 13) |
| β₇D1 | YRLSVEIYDRREYSRFEKEQQQLNWKQDSNP | (SEQ ID NO: 14) |
| β₇D2 | YRLSVEIYDRREYSRFEKEQQQLNWKQDSNPLYKSA | (SEQ ID NO: 15) |
| β₇D3 | YRLSVEIYDRREYSRFEKEQQQLNWKQDSNPLYKSAITTTINP | (SEQ ID NO: 16) |
| β₇D4 | YRLSVEIYDRREYSRFEKE | (SEQ ID NO: 17) |
| β₇D5 | YRLSVEIYDRREYSR | (SEQ ID NO: 18) |
| β₇D6 | YRLSVEIYDRR | (SEQ ID NO: 39) |
| β₇D8 | YRLSVEIYDRREYSRFEKEQQQLNWKQDSNPLYKSAITTTINPRFQEAD | (SEQ ID NO: 40) |
| β₇D9 | YRLSVEIYDRREYSRFEKEQQQLNWKQDSNPLYKSAITTTINPRF | (SEQ ID NO: 41) |

Primers used to generate the various deletion mutants are set out in SEQ ID NOs: 19 to 23 and 42–46, below, and were individually utilized in an amplification reaction pairs with the primer set out in SEQ ID NO: 3. Reaction conditions were as described in Example 1. Deletions β₇D8 and β₇D9 were prepared using Quickchange site directed mutagenesis (Stratagene, La Jolla, Calif.) and all other deletions were prepared by standard single stranded site directed mutagenesis.

| | | | |
|---|---|---|---|
| NHβ₇D1 | GATGGCACTTTTGTACTAAGGATTACTGTCCTG | | (SEQ ID NO: 19) |
| NHβ₇D2 | ATTGATGGTGGTCGTCTAGGCACTTTTGTAGAG | | (SEQ ID NO: 20) |
| NHβ₇D3 | GTCTGCCTCTTGAAACTAAGGATTGATGGTGGT | | (SEQ ID NO: 21) |
| NHβ₇D4 | CCAGTTGAGTTGTTGCTACTCCTTCTCAAAGCG | | (SEQ ID NO: 22) |
| NHβ₇D5 | GTTGCTGCTCCTTCTCCTAGCGACTGTATTCCCG | | (SEQ ID NO: 23) |
| β₇D6: | CTCAAAGCGACTGTACTACCGGCGGTCATAGATTTC | | (SEQ ID NO: 42) |
| β₇D8: | CTTTCAAGAGGCAGACTGACCCACTCTCTGAGGA | (sense oligo) | (SEQ ID NO: 43) |
| β₇D8: | TCCTCAGAGAGTGGGTCAGTCTGCCTCTTGAAAG | (antisense oligo) | (SEQ ID NO: 44) |
| β₇D9: | CATCAATCCTCGCTTTTGAGAGGCAGACAGTCCC | (sense oligo) | (SEQ ID NO: 45) |
| β₇D9: | GGGACTGTCTGCCTCTCAAAAGCGAGGATTGATC | (antisense oligo) | (SEQ ID NO: 46) |

In addition, a series of β₇ substitution mutants were also constructed wherein the sequence changes are set out in SEQ ID NOs: 24 to 27 and 47–51, with the substituted amino acid residue underlined.

| | | |
|---|---|---|
| β₇S3A | YRL<u>A</u>VEIYDRREYSRFEKEQQQLNWKQDSNPLYKSAITTTINPRFQEADSPTL | (SEQ ID NO: 24) |
| β₇E5Q | YRLSV<u>Q</u>IYDRREYSRFEKEQQQLNWKQDSNPLYKSAITTTINPRFQEADSPTL | (SEQ ID NO: 25) |
| β₇R9A | YRLSVEIYD<u>A</u>REYSRFEKEQQQLNWKQDSNPLYKSAITTTINPRFQEADSPTL | (SEQ ID NO: 26) |
| β₇S13A | YRLSVEIYDRREY<u>A</u>RFEKEQQQLNWKQDSNPLYKSAITTTINPRFQEADSPTL | (SEQ ID NO: 27) |
| β₇V4F | YRLS<u>F</u>EIYDRREYSRFEKEQQQLNWKQDSNPLYKSAITTTINPRFQEADSPTL | (SEQ ID NO: 47) |
| β₇I6F | YRLSVE<u>F</u>YDRREYSRFEKEQQQLNWKQDSNPLYKSAITTTINPRFQEADSPTL | (SEQ ID NO: 48) |
| β₇Y7F | YRLSVEI<u>F</u>DRREYSRFEKEQQQLNWKQDSNPLYKSAITTTINPRFQEADSPTL | (SEQ ID NO: 49) |
| β₇D8A | YRLSVEIY<u>A</u>RREYSRFEKEQQQLNWKQDSNPLYKSAITTTINPRFQEADSPTL | (SEQ ID NO: 50) |

-continued

| | | |
|---|---|---|
| β₇R10A | YRLSVEIYDR<u>A</u>EYSRFEKEQQQLNWKQDSNPLYKSAITTTINPRFQEADSPTL | (SEQ ID NO: 51) |

Oligonucleotides used to generate the various substitution variants are set out in SEQ ID NOs: 28 to 31 and 52 to 56, infra.

| | | |
|---|---|---|
| B7S3A | GTCATAGATTTCCACCGCGAGCCGGTATCCGAG | (SEQ ID NO: 28) |
| B7E5Q | CCGGCCGTCATAGATTTGCACCGAGAGCCGGTATC | (SEQ ID NO: 29) |
| B7R9A | GCGACTGTATTCCCGCGCGTCATAGATTTCCAC | (SEQ ID NO: 30) |
| B7S13A | CTCCTTCTCAAAGCGCGTATTCCCGGCGGTC | (SEQ ID NO: 31) |
| β₇V4F | GCGGTCATAGATTTCAAACGAGAGCCGGTATCC | (SEQ ID NO: 52) |
| β₇I6F | TTCCCGGCGGTCATAGAATTCCACCGAGAGCCG | (SEQ ID NO: 53) |
| β₇Y7F | GTATTCCCGGCGGTCAAAGATTTCCACCGAGAG | (SEQ ID NO: 54) |
| β₇D8A | ACTGTATTCCCGGCGCGCATAGATTTCCACCGA | (SEQ ID NO: 55) |
| β₇R10A | AAAGCGACTGTATTCCGCGCGGTCATAGATTTC | (SEQ ID NO: 56) |

Specific truncation mutants of filamin were generated by PCR amplification of existing clones under conditions described in Example 1. Mutant ABPD1 encoded a region including a portion of repeat 23, the second hinge region and repeat 24 of filamin (amino acid 2487–2647 in SEQ ID NO: 7). Mutant ABPD2 (amino acids 2487–2577 in SEQ ID NO: 7) encoded a truncated form of ABPD1 which lacked the filamin dimerization domain. Mutant ABPD4 (amino acids 2517–2647 in SEQ ID NO: 7) encoded a truncated form of ABPD1 which lacked the twenty-third repeat. Mutant ABPD5 (amino acid 2198–2435 in SEQ ID NO: 7) encoded a truncated form of clone 411 which lacked most of repeat 23, the second hinge region and repeat 24. Mutant ABPD9 (amino acid 2350–2435 in SEQ ID NO:7) encoded a truncated form of ABPD5. Mutant ABPD10 (amino acid 2256–2363 in SEQ ID NO: 7) encoded another truncated form of ABPD5.

Mutant ABPD1 was generated by PCR using primers set out in SEQ ID NO: 32 and 33, and mutant ABPD2 was generated by PCR using primers set out in SEQ ID NO: 32 and 34.

Primers 32–34 were used in a reaction with filamin clone 1271 under the following amplification conditions: an initial incubation at 94° C. for five minutes, followed by thirty cycles of 94° C. for 30 seconds, 50° C. for 30 seconds, and 72° C. for one minute. The resulting PCR product was cut with Xho1 and ligated into vector pACT (described in Example 1) previously digested with Xho1.

Mutants ABPD4, ABPD5, ABPD9 and ABPD10 were generated by PCR. ABPD4 was generated using primers 1271/151 and 1271/3XR and used clone 1271 as the DNA template. ABPD5 was generated using primers B7411/1X and B7411/700X and used clone 411 as the DNA template. ABPD9 was generated using primers B7411/457X and B7411/700X and used clone 411 as the DNA template. ABPD10 was generated using primers B7411/175X and B7411/498X and used clone 411 as the DNA template.

| | | |
|---|---|---|
| ABP.5x | ATATCTCGAGAGTATACCCCCATGGCACCT | (SEQ ID NO: 32) |
| ABP.Xho1 | ATATCTCGAGTCAGGGCACCACAACGCG | (SEQ ID NO: 33) |
| ABP.Xho2 | ATATCTCGAGTCAGCTGCTCTTCTGGCCCTAC | (SEQ ID NO: 34) |

| | | |
|---|---|---|
| 1271/151 | CCCGAATTCACAGGCCCCCGTCTCGTC | (SEQ ID NO: 57) |
| 1271/3XR | CCCGAATTCCTCGAGTCAGGGCACCACAACGCGGTAG | (SEQ ID NO: 58) |
| B7411/1X | CCCCCTCGAGGCTACTGCATCCGCTTTGTTC | (SEQ ID NO: 59) |
| B7411/700X | CCCCTCGAGTCAGTAAGCAGACACCAAGCC | (SEQ ID NO: 60) |
| B7411/457X | CCCCTCGAGCCAGCCTCTTTTGCAGTC | (SEQ ID NO: 61) |
| B7411/175X | CCCCTCGAGCCAGCCGAATTCAGTATC | (SEQ ID NO: 62) |
| B7411/498X | CCCCTCGAGTCACGCCCCCTTGGCCCCCTTC | (SEQ ID NO: 63) |

Primers as described were used in PCR reactions with the appropriate templates under amplification conditions outlined in Example 1. The resulting PCR products were cut with XhoI (ABPD5, ABPD9 and ABPD10) or EcoRI (ABPD4) and ligated into vector pACT (ABPD5) or vector pACT2 (ABPD9 and ABPD10) previously digested with XhoI or ligated into vector pGAD10 (ABPD4) previously digested with EcoRI. The resulting subclones were sequenced to rule out PCR derived errors.

An FLP-1 mutant comprised of amino acid sequences 696 to 857 in SEQ ID NO: 1 and showing identity to TABP (the TABP-like analog) was also generated by PCR amplification (under conditions described in Example 1) from a human spleen cDNA library. The FLP-1 mutant was generated by PCR using the primer pair set out in SEQ ID NO: 35 and 36.

TABP.Nde    ATATCATATGTACACCCCCATGGCTCCT (SEQ ID NO: 35)

TABP.Bam    ATAGGATCCTCAGCCCCACAAACAGGC (SEQ ID NO: 36)

Reactions were carried out using 2.5 μg spleen cDNA under the following amplification conditions: an initial incubation at 94° C. for five minutes, followed by thirty cycles of 94° C. for 30 seconds, 50° C. for 30 seconds, and 72° C. for one minute. The resulting PCR products were digested with NdeI and BamHI and cloned into vector pET previously digested with the same enzymes. The resulting TABP/pET vector was then utilized in a secondary PCR with the PCR primer pair set out in SEQ ID NO: 32 and 33, above, under the following conditions: an initial incubation at 94° C. for five minutes, followed by thirty cycles at 94° for one minute, 50° C. for one minute and 72° C. for two minutes. The resulting PCR product was digested with Xho1 and cloned into pACT previously digested with Xho1. The FLP-1 TABP-like truncate represents the same size and region in filamin as represented by mutant ABPD1.

Another FLP-1 mutant, FLP1D3, was generated by PCR. FLPlD3 encoded a truncated form of clone S5 (amino acid 272–483 in SEQ ID NO:11). FLP1D3 represents the carboxy terminal region of S5, which is not encoded by S3. The primers used to generate this mutant were B7S5/814X and B7S5/1475X and clone S5 was used as the DNA template.

B7S5/814X   CCCCCTCGAGGCGGCACGGGACTCGAAGGG (SEQ ID NO: 64)

B7S5/1475X  CCCCTCGAGTTAAGGCACTGTGACATG   (SEQ ID NO: 65)

These primers were utilized in PCR reactions under amplification conditions outlined in Example 1. The resulting PCR products were digested with AoI and ligated into the vector pACT previously digested with )aoI. Sequencing of the resulting subclones ruled out PCR derived errors.

Results from the two hybrid assays as shown in Tables 2–4, discussed below, indicate that there are two distinct regions of filamin capable of interacting with the $\beta_7$ cytoplasmic tail. The first region is represented by clones 514 and 1271, the second region by deletion mutant ABPD5. In the first binding region of filamin (as represented by clones 514 and 1271) the dimerization domain (amino acids 2578–2647 of SEQ ID NO: 7) (not present in ABPD2) and the region at the 5' end of repeat 23 (not present in ABPD4) appear to be critical for interaction with the $\beta_7$ cytoplasmic tail. The results with TABP and FLP1D3 also show that despite a high degree of homology with filamin, there does not appear to be a corresponding region in FLP-1 similar to the "repeat 23–24" region found in filamin clones 514 and 1271 which is capable of interacting with the $\beta_7$ cytoplasmic tail. In addition, interaction with ABPD5 indicates a second region of filamin centered around repeat 21 which interacts with the $\beta_7$ cytoplasmic tail, corresponding to a region of FLP-1 (amino acid 1–273 of SEQ ID NO: 12), and is most likely to be responsible for the FLP-1 interaction with $\beta_7$ cytoplasmic tail.

TABLE 2

INTERACTION OF FILAMIN (1271)
AND FLP-1 (S5) WITH $\beta_7$ DELETION AND
SUBSTITUTION ANALOGS

| | FILAMIN | ABPD1 | ABPD2 | FLP-1 | TABP |
|---|---|---|---|---|---|
| $\beta_2$ | − | − | − | − | − |
| $\beta_7$ | + | +/− | − | + | − |
| $\beta_7$D1 | + | + | − | +/− | |
| $\beta_7$D2 | + | + | − | +/− | |
| $\beta_7$D3 | + | + | − | + | |
| $\beta_7$D4 | + | + | − | + | |
| $\beta_7$D5 | + | + | | + | |
| $\beta_7$S3A | + | + | | + | |
| $\beta_7$E5Q | +/− | +/− | | + | |
| $\beta_7$R9A | + | + | | + | |
| $\beta_7$S13A | + | + | | + | |
| $\alpha_L$ | − | | | − | − |

TABLE 3

INTERACTION OF $\beta_7$ WITH FILAMIN
AND FLP-1 AND DELETION MUTANTS

| | $\beta_7$ |
|---|---|
| FILAMIN | |
| 1271 | + |
| 514 | + |
| 411 | + |
| ABPD1 | +/− |
| ABPD2 | − |
| ABPD4 | − |
| ABPD5 | + |
| ABPD9 | − |

TABLE 3-continued

INTERACTION OF $\beta_7$ WITH FILAMIN
AND FLP-1 AND DELETION MUTANTS

| | $\beta_7$ |
|---|---|
| ABPD10 | − |
| FLP-1 | |
| S3 | + |
| S5 | + |
| TABP | − |
| FLP1D3 | − |

Table 2 and Table 4 below summarize the effect of $\beta_7$ deletion mutants and substitution analogs on binding of $\beta_7$ to filamin (clone 514), ABPD1, ABPD2, ABPD5, TABP and FLP-1 clones S3 and S5. The binding properties of the first filamin binding site, represented by clones 514 and 1271, is affected by substitutions in the membrane proximal region of the $\beta_7$ cytoplasmic tail. Specifically, substitution mutant E5Q greatly weakens the interaction with clones 514 and 1271. Substitution mutant D8A completely disrupts the interaction of $\beta_7$ with clones 514 and 1271 (Table 4). The binding of ABPD5 to $\beta_7$ (the second region of filamin which interacts with the $\beta_7$ cytoplasmic tail) is not affected by substitutions in the membrane proximal region of the $\beta_7$ cytoplasmic tail, as shown by substitution mutants E5Q and D8A. However, the binding of ABPD5 to $\beta_7$ is decreased in deletion mutants at the carboxy terminus of the $\beta_7$ cytoplasmic tail, as shown by deletion mutants $\beta_7$D1 and $\beta_7$D2 (Table 4). FFLP-1 clones S3 and S5 demonstrate a pattern of interaction with the $\beta_7$ deletion and substitution mutants that is remarkably similar to ABPD5. Because ABPD5, S3 and S5 were able to interact with deletion mutants smaller than $\beta_7$D1 and $\beta_7$D2, such as $\beta_7$D6, it is possible that this region of filamin or FLP-1 can interact with more than one region of the $\beta_7$ cytoplasmic tail.

TABLE 4

INTERACTION OF
FILAMIN (514) WITH $\beta_7$ DELETION
AND SUBSTITUTION ON ANALOGS

| | 514 | ABPD5 | S3 | S5 |
|---|---|---|---|---|
| $\beta_7$ | + | + | + | + |
| $\beta_7$D1 | + | +/− | +/− | +/− |
| $\beta_7$D2 | + | +/− | +/− | +/− |
| $\beta_7$D4 | + | + | | + |
| $\beta_7$D5 | + | + | | + |
| $\beta_7$D6 | + | + | + | +/− |
| $\beta_7$D8 | +/− | + | + | + |
| $\beta_7$D9 | + | + | + | + |
| $\beta_7$S3A | + | + | | + |
| $\beta_7$V4F | + | | | + |
| $\beta_7$E5Q | +/− | + | + | + |
| $\beta_7$I6F | + | | | + |
| $\beta_7$Y7F | + | + | | + |
| $\beta_7$D8A | − | + | + | + |
| $\beta_7$R9A | + | + | | + |
| $\beta_7$S13A | + | | | + |

The data presented in this Example demonstrates that there are two distinct regions of filamin which interact with two distinct regions of the $\beta_7$ cytoplasmic tail. They also show that the region of FLP-1 which interacts with the $\beta_7$ cytoplasmic tail is similar to the ABPD5 region of filamin in its interaction characteristics with the $\beta_7$ cytoplasmic tail.

EXAMPLE 6

Applications for Modulators of Filamin/$\beta_7$ and FLP-1/$\beta_7$ Binding

Two $\beta_7$ associated integrins have been identified: $\alpha_4\beta_7$ and $\alpha_E\beta_7$. Both are expressed on a subpopulation of peripheral blood lymphocytes and their expression is inducible. Both are expressed on macrophages but not monocytes and both appear to function in homing or localization of lymphocytes to mucosal tissue [see review in Jutila, J. *Leukocyte Biol.* 55:133–140 (1994)]. The homing properties of $\alpha_4\beta_7$ can be attributed to interaction with MadCAM-1 expressed in mucosal nodes, while the retention of $\alpha_E\beta_7^+$ cells in the gut is attributed to interactions with epithelial cells expressing E-cadherin. Thus, binding by one or both $\beta_7$ integrins to their respective counter-receptor may contribute to mucosal immune responses as well as inflammatory (e.g., inflammatory bowel disease, IIBD) and autoimmune responses at this site.

Further, it has been suggested that filamin is important in cell locomotion due to the fact that cells expressing low levels of the protein do not form leading lamella structures required for locomotion. The structural homology of FLP-1 to filamin suggests a similar role for this protein. In view of the observation that integrins can be observed clustered in point contacts, which are also important in cell locomotion, the invention contemplates that $\beta_7$ interaction with FLP-1 and/or filamin may be crucial to cell movement, and that disruption of the interactions will be useful, for example, in preventing the homing of $\beta_7^+$ cells which occurs in certain pathological inflammatory responses such as IBD.

In order to identify modulators of $\beta_7$/FLP-1 interaction, it is necessary to clearly define the portions of both proteins which are necessary for binding. Amino acid substitution, through standard mutagenesis techniques will permit identification of the binding regions of the proteins. Deletion analysis, wherein truncated forms of either protein are generated, for example by PCR, is also useful for identification of binding regions if the deletion does not disrupt the tertiary or quaternary structure of the protein to the point that it is no longer recognized buy its counter-receptor.

Identification of the significant protein regions involved in binding permits more accurate and efficient screening of putative modulators of binding activity. The invention contemplates of a high throughput screening assay to analyze large libraries of small molecules or peptides, as well as antibodies immunospecific for either or both binding partners, for the ability to modulate binding of $\beta_7$ integrins to FLP-1 or filamin. While two hybrid screening, scintillation proximity assays (SPA) and immunological methodologies, for example, enzyme-linked immunosorbent assays (FLISA), disclosed herein are not HTS methods per se, they are amenable to test many of the compounds listed for an ability to modulate binding. SPA and ELISA are particularly useful in this identification process and can be modified to permit high throughput screening of the test compounds described.

What is claimed is:

1. A purified and isolated $\beta_7$ integrin cytoplasmic domain-binding FLP-1 (filamin-like binding protein) polypeptide having the amino acid sequence set out in SEQ ID NO: 2.

2. A purified and isolated $\beta_7$ integrin cytoplasmic domain-binding FLP-1 polypeptide encoded by a DNA selected from the group consisting of:

a) the human DNA sequence set out in SEQ ID NO:1;

b) a DNA molecule which hybridizes under stringent conditions to the noncoding strand of the protein coding portion of (a); and c) a DNA molecule that would hybridize to the DNA of (a) but for the degeneracy of the genetic code.

* * * * *

UNITED STATES PATENT AND TRADEMARK OFFICE
CERTIFICATE OF CORRECTION

PATENT NO. : 5,948,891

DATED : September 7, 1999

INVENTOR(S) : Staunton et al.

Page 1 of 2

It is certified that error appears in the above-identified patent and that said Letters Patent is hereby corrected as shown below:

On the title page: Item

References Cited, U.S. PATENT DOCUMENTS, "5,506,126  4/1996  Seed et al." should be -- 5,506,126  5/1996  Seed et al.--

Column 1, line 55, "205:32767" should be --205:282-293--.

Column 2, line 10, "also know" should be --also known--.

Column 2, line 38, after "tissues" add --(--.

Column 2, line 46, "$\beta$-actinin" should be --$\alpha$-actinin--.

Column 3, line 7, "et aL," should be --et al.,--

Column 3, line 26, "u integrin-mediated" should be --$\alpha_4$ integrin-mediated--.

Column 6, line 56, "tail/HA/GALA" should be --tail/HA/GAL4--.

Column 6, line 59, "GALA" should be --GAL4--.

Column 7, line 16, "7552, 7579, and 7579" should be --7552, and 7579--.

Column 7, line 23, "amino acids sequences" should be --amino acid sequences--.

Column 8, line 13, "MRNA" should be --mRNA--.

Column 8, line 54, "is changed G" should be --is changed to G--.

Column 8, line 66, "MRNA" should be --mRNA--.

Column 9, line 16, "MRNA" should be --mRNA--.

Column 9, line 35, "northems" should be --northerns--.

UNITED STATES PATENT AND TRADEMARK OFFICE
CERTIFICATE OF CORRECTION

PATENT NO. : 5,948,891

DATED : September 7, 1999

INVENTOR(S) : Staunton et al.

It is certified that error appears in the above-identified patent and that said Letters Patent is hereby corrected as shown below:

Column 15, line 54, "AoI" should be --XhoI--. (p. 23, l. 5)

Column 15, line 55, ")aoi" shoudl be --XhoI--. (p. 23, l. 6)

Column 18, line 21, "IIBD" should be --IBD--. (p. 27, l. 14)

Signed and Sealed this

Seventeenth Day of April, 2001

*Attest:*

NICHOLAS P. GODICI

*Attesting Officer*     *Acting Director of the United States Patent and Trademark Office*

SEQUENCE LISTING (1) GENERAL INFORMATION:

(iii) NUMBER OF SEQUENCES: 65

(2) INFORMATION FOR SEQ ID NO:1:

(i) SEQUENCE CHARACTERISTICS:
      (A) LENGTH: 2574 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..2574

(xi) SEQUENCE DESCRIPTION: SEQ ID NO:1:

```
CCT TTT GAC CTG GTC ATT CCG TTT GCT GTC AGG AAA GGA GAA ATC ACT        48
Pro Phe Asp Leu Val Ile Pro Phe Ala Val Arg Lys Gly Glu Ile Thr
 1               5                  10                  15

GGA GAG GTC CAC ATG CCT TCT GGG AAG ACA GCC ACA CCT GAG ATT GTG        96
Gly Glu Val His Met Pro Ser Gly Lys Thr Ala Thr Pro Glu Ile Val
                20                  25                  30

GAC AAC AAG GAC GGC ACG GTC ACT GTT AGA TAT GCC CCC ACT GAG GTC       144
Asp Asn Lys Asp Gly Thr Val Thr Val Arg Tyr Ala Pro Thr Glu Val
            35                  40                  45

GGG CTC CAT GAG ATG CAC ATC AAA TAC ATG GGC AGC CAC ATC CCT GAG       192
Gly Leu His Glu Met His Ile Lys Tyr Met Gly Ser His Ile Pro Glu
        50                  55                  60

AGC CCA CTC CAG TTC TAC GTG AAC TAC CCC AAC AGT GGA AGT GTT TCT       240
Ser Pro Leu Gln Phe Tyr Val Asn Tyr Pro Asn Ser Gly Ser Val Ser
 65                  70                  75                  80

GCA TAC GGT CCA GGC CTC GTG TAT GGA GTG GCC AAC AAA ACT GCC ACC       288
Ala Tyr Gly Pro Gly Leu Val Tyr Gly Val Ala Asn Lys Thr Ala Thr
                85                  90                  95

TTC ACC ATC GTC ACA GAG GAT GCA GGA GAA GGT GGT CTG GAC TTG GCT       336
Phe Thr Ile Val Thr Glu Asp Ala Gly Glu Gly Gly Leu Asp Leu Ala
            100                 105                 110

ATT GAG GGC CCC TCA AAA GCA GAA ATC AGC TGC ATT GAC AAT AAA GAT       384
Ile Glu Gly Pro Ser Lys Ala Glu Ile Ser Cys Ile Asp Asn Lys Asp
        115                 120                 125

GGG ACA TGC ACA GTG ACC TAC CTG CCG ACT CTG CCA GGC GAC TAC AGC       432
Gly Thr Cys Thr Val Thr Tyr Leu Pro Thr Leu Pro Gly Asp Tyr Ser
    130                 135                 140

ATT CTG GTC AAG TAC AAT GAC AAG CAC ATC CCT GGC AGC CCC TTC ACA       480
Ile Leu Val Lys Tyr Asn Asp Lys His Ile Pro Gly Ser Pro Phe Thr
145                 150                 155                 160

GCC AAG ATC ACA GAT GAC AGC AGG CGG TGC TCC CAG GTG AAG TTG GGC       528
Ala Lys Ile Thr Asp Asp Ser Arg Arg Cys Ser Gln Val Lys Leu Gly
                165                 170                 175

TCA GCC GCT GAC TTC CTG CTC GAC ATC AGT GAG ACT GAC CTC AGC AGC       576
Ser Ala Ala Asp Phe Leu Leu Asp Ile Ser Glu Thr Asp Leu Ser Ser
            180                 185                 190

CTG ACG GCC AGC ATT AAG GCC CCA TCT GGC CGA GAC GAG CCC TGT CTC       624
Leu Thr Ala Ser Ile Lys Ala Pro Ser Gly Arg Asp Glu Pro Cys Leu
        195                 200                 205

CTG AAG AGG CTG CCC AAC AAC CAC ATT GGC ATC TCC TTC ATC CCC CGG       672
Leu Lys Arg Leu Pro Asn Asn His Ile Gly Ile Ser Phe Ile Pro Arg
    210                 215                 220
```

-continued

| | | |
|---|---|---|
| GAA GTG GGC GAA CAT CTG GTC AGC ATC AAG AAA AAT GGC AAC CAT GTG<br>Glu Val Gly Glu His Leu Val Ser Ile Lys Lys Asn Gly Asn His Val<br>225                             230                           235                       240 | 720 | |
| GCC AAC AGC CCC GTG TCT ATC ATG GTG GTC CAG TCG GAG ATT GGT GAC<br>Ala Asn Ser Pro Val Ser Ile Met Val Val Gln Ser Glu Ile Gly Asp<br>                 245                          250                         255 | 768 | |
| GCC CGC CGA GCC AAA GTC TAT GGC CGC GGC CTG TCA GAA GGC CGG ACT<br>Ala Arg Arg Ala Lys Val Tyr Gly Arg Gly Leu Ser Glu Gly Arg Thr<br>        260                           265                         270 | 816 | |
| TTC GAG ATG TCT GAC TTC ATC GTG GAC ACA AGG GAT GCA GGT TAT GGT<br>Phe Glu Met Ser Asp Phe Ile Val Asp Thr Arg Asp Ala Gly Tyr Gly<br>               275                          280                         285 | 864 | |
| GGC ATA TCC TTG GCG GTG GAA GGC CCC AGC AAA GTG GAC ATC CAG ACG<br>Gly Ile Ser Leu Ala Val Glu Gly Pro Ser Lys Val Asp Ile Gln Thr<br>290                             295                           300 | 912 | |
| GAG GAC CTG GAA GAT GGC ACC TGC AAA GTC TCC TAC TTC CCT ACC GTG<br>Glu Asp Leu Glu Asp Gly Thr Cys Lys Val Ser Tyr Phe Pro Thr Val<br>305                             310                         315               320 | 960 | |
| CCT GGG GTT TAT ATC GTC TCC ACC AAA TTC GCT GAC GAG CAC GTG CCT<br>Pro Gly Val Tyr Ile Val Ser Thr Lys Phe Ala Asp Glu His Val Pro<br>                 325                          330                         335 | 1008 | |
| GGG AGC CCA TTT ACC GTG AAG ATC AGT GGG GAG GGA AGA GTC AAA GAG<br>Gly Ser Pro Phe Thr Val Lys Ile Ser Gly Glu Gly Arg Val Lys Glu<br>        340                         345                         350 | 1056 | |
| AGC ATC ACC CGC ACC AGT CGG GCC CCG TCC GTG GCC ACT GTC GGG AGC<br>Ser Ile Thr Arg Thr Ser Arg Ala Pro Ser Val Ala Thr Val Gly Ser<br>               355                          360                         365 | 1104 | |
| ATT TGT GAC CTG AAC CTG AAA ATC CCA GAA ATC AAC AGC AGT GAT ATG<br>Ile Cys Asp Leu Asn Leu Lys Ile Pro Glu Ile Asn Ser Ser Asp Met<br>370                             375                         380 | 1152 | |
| TCG GCC CAC GTC ACC AGC CCC TCT GGC CGT GTG ACT GAG GCA GAG ATT<br>Ser Ala His Val Thr Ser Pro Ser Gly Arg Val Thr Glu Ala Glu Ile<br>385                             390                         395               400 | 1200 | |
| GTG CCC ATG GGG AAG AAC TCA CAC TGC GTC CGG TTT GTG CCC CAG GAG<br>Val Pro Met Gly Lys Asn Ser His Cys Val Arg Phe Val Pro Gln Glu<br>                       405                         410                       415 | 1248 | |
| ATG GGC GTG CAC ACG GTC AGC GTC AAG TAC CGT GGG CAG CAC GTC ACC<br>Met Gly Val His Thr Val Ser Val Lys Tyr Arg Gly Gln His Val Thr<br>                      420                          425                       430 | 1296 | |
| GGC AGC CCC TTC CAG TTC ACC GTG GGG GCA CTT GGT GAA GGA GGC GCC<br>Gly Ser Pro Phe Gln Phe Thr Val Gly Ala Leu Gly Glu Gly Gly Ala<br>               435                          440                         445 | 1344 | |
| CAC AAG GTG CGG GCA GGA GGC CCT GGC CTG GAG AGA GGA GAA GCG GGA<br>His Lys Val Arg Ala Gly Gly Pro Gly Leu Glu Arg Gly Glu Ala Gly<br>450                             455                         460 | 1392 | |
| GTC CCA GCT GAG TTC AGC ATT TGG ACC CGG GAA GCA GGC GCT GGA GGC<br>Val Pro Ala Glu Phe Ser Ile Trp Thr Arg Glu Ala Gly Ala Gly Gly<br>465                             470                         475               480 | 1440 | |
| CTC TCC ATC GCT GTT GAG GGC CCC AGT AAG GCC GAG ATT ACA TTC GAT<br>Leu Ser Ile Ala Val Glu Gly Pro Ser Lys Ala Glu Ile Thr Phe Asp<br>                      485                         490                     495 | 1488 | |
| GAC CAT AAA AAT GGG TCG TGC GGT GTA TCT TAT ATT GCC CAA GAG CCT<br>Asp His Lys Asn Gly Ser Cys Gly Val Ser Tyr Ile Ala Gln Glu Pro<br>               500                          505                         510 | 1536 | |
| GGT AAC TAC GAG GTG TCC ATC AAG TTC AAT GAT GAG CAC ATC CCG GAA<br>Gly Asn Tyr Glu Val Ser Ile Lys Phe Asn Asp Glu His Ile Pro Glu<br>               515                          520                         525 | 1584 | |
| AGC CCC TAC CTG GTG CCG GTC ATC GCA CCC TCC GAC GAC GCC CGC CGC<br>Ser Pro Tyr Leu Val Pro Val Ile Ala Pro Ser Asp Asp Ala Arg Arg<br>530                             535                           540 | 1632 | |

```
CTC ACT GTT ATG AGC CTT CAG GAA TCG GGA TTA AAA GTT AAC CAG CCA    1680
Leu Thr Val Met Ser Leu Gln Glu Ser Gly Leu Lys Val Asn Gln Pro
545                 550                 555                 560

GCA TCC TTT GCT ATA AGG TTG AAT GGC GCA AAA GGC AAG ATT GAT GCA    1728
Ala Ser Phe Ala Ile Arg Leu Asn Gly Ala Lys Gly Lys Ile Asp Ala
                565                 570                 575

AAG GTG CAC AGC CCC TCT GGA GCC GTG GAG GAG TGC CAC GTG TCT GAG    1776
Lys Val His Ser Pro Ser Gly Ala Val Glu Glu Cys His Val Ser Glu
            580                 585                 590

CTG GAG CCA GAT AAG TAT GCT GTT CGC TTC ATC CCT CAT GAG AAT GGT    1824
Leu Glu Pro Asp Lys Tyr Ala Val Arg Phe Ile Pro His Glu Asn Gly
        595                 600                 605

GTC CAC ACC ATC GAT GTC AAG TTC AAT GGG AGC CAC GTG GTT GGA AGC    1872
Val His Thr Ile Asp Val Lys Phe Asn Gly Ser His Val Val Gly Ser
    610                 615                 620

CCC TTC AAA GTG CGC GTT GGG GAG CCT GGA CAA GCG GGG AAC CCT GCC    1920
Pro Phe Lys Val Arg Val Gly Glu Pro Gly Gln Ala Gly Asn Pro Ala
625                 630                 635                 640

CTG GTG TCC GCC TAT GGC ACG GGA CTC GAA GGG GGN ACC ACA GGT ATC    1968
Leu Val Ser Ala Tyr Gly Thr Gly Leu Glu Gly Xaa Thr Thr Gly Ile
                645                 650                 655

CAG TCG GAA TTC TTT ATT AAC ACC ACC CGA GCA GGT CCA GGG ACA TTA    2016
Gln Ser Glu Phe Phe Ile Asn Thr Thr Arg Ala Gly Pro Gly Thr Leu
                660                 665                 670

TCC GTC ACC ATC GAA GGC CCA TCC AAG GTT AAA ATG GAT TGC CAG GAA    2064
Ser Val Thr Ile Glu Gly Pro Ser Lys Val Lys Met Asp Cys Gln Glu
            675                 680                 685

ACA CCT GAA GGG TAC AAA GTC ATG TAC ACC CCC ATG GCT CCT GGT AAC    2112
Thr Pro Glu Gly Tyr Lys Val Met Tyr Thr Pro Met Ala Pro Gly Asn
        690                 695                 700

TAC CTG ATC AGT GTC AAA TAC GGT GGG CCC AAC CAC ATC GTG GGC AGT    2160
Tyr Leu Ile Ser Val Lys Tyr Gly Gly Pro Asn His Ile Val Gly Ser
705                 710                 715                 720

CCC TTC AAG GCC AAG GTG ACT GGC CAG CGT CTA GTT AGC CCT GGC TCA    2208
Pro Phe Lys Ala Lys Val Thr Gly Gln Arg Leu Val Ser Pro Gly Ser
                725                 730                 735

GCC AAC GAG ACC TCA TCC ATC CTG GTG GAG TCA GTG ACC AGG TCG TCT    2256
Ala Asn Glu Thr Ser Ser Ile Leu Val Glu Ser Val Thr Arg Ser Ser
                740                 745                 750

ACA GAG ACC TGC TAT AGC GCC ATT CCC AAG GCA TCC TCG GAC GCC AGC    2304
Thr Glu Thr Cys Tyr Ser Ala Ile Pro Lys Ala Ser Ser Asp Ala Ser
            755                 760                 765

AAG GTG ACC TCT AAG GGG GCA GGG CTC TCA AAG GCC TTT GTG GGC CAG    2352
Lys Val Thr Ser Lys Gly Ala Gly Leu Ser Lys Ala Phe Val Gly Gln
        770                 775                 780

AAG AGT TCC TTC CTG GTG GAC TGC AGC AAA GCT GGC TCC AAC ATG CTG    2400
Lys Ser Ser Phe Leu Val Asp Cys Ser Lys Ala Gly Ser Asn Met Leu
785                 790                 795                 800

CTG ATC GGG GTC CAT GGG CCC ACC ACC CCC TGC GAG GAG GTC TCC ATG    2448
Leu Ile Gly Val His Gly Pro Thr Thr Pro Cys Glu Glu Val Ser Met
                805                 810                 815

AAG CAT GTA GGC AAC CAG CAA TAC AAC GTC ACA TAC GTC GTC AAG GAG    2496
Lys His Val Gly Asn Gln Gln Tyr Asn Val Thr Tyr Val Val Lys Glu
                820                 825                 830

AGG GGC GAT TAT GTG CTG GCT GTG AAG TGG GGG GAG GAA CAC ATC CCT    2544
Arg Gly Asp Tyr Val Leu Ala Val Lys Trp Gly Glu Glu His Ile Pro
            835                 840                 845

GGC AGC CCT TTT CAT GTC ACA GTG CCT TAA                            2574
Gly Ser Pro Phe His Val Thr Val Pro
850                 855
```

(2) INFORMATION FOR SEQ ID NO:2:

(i) SEQUENCE CHARACTERISTICS:
        (A) LENGTH: 857 amino acids
        (B) TYPE: amino acid
        (D) TOPOLOGY: Not Relevant (ii) MOLECULE TYPE: protein (xi) SEQUENCE DESCRIPTION: SEQ ID NO:2:

```
Pro Phe Asp Leu Val Ile Pro Phe Ala Val Arg Lys Gly Glu Ile Thr
 1               5                  10                  15

Gly Glu Val His Met Pro Ser Gly Lys Thr Ala Thr Pro Glu Ile Val
             20                  25                  30

Asp Asn Lys Asp Gly Thr Val Thr Val Arg Tyr Ala Pro Thr Glu Val
         35                  40                  45

Gly Leu His Glu Met His Ile Lys Tyr Met Gly Ser His Ile Pro Glu
     50                  55                  60

Ser Pro Leu Gln Phe Tyr Val Asn Tyr Pro Asn Ser Gly Ser Val Ser
65                  70                  75                  80

Ala Tyr Gly Pro Gly Leu Val Tyr Gly Val Ala Asn Lys Thr Ala Thr
                 85                  90                  95

Phe Thr Ile Val Thr Glu Asp Ala Gly Glu Gly Gly Leu Asp Leu Ala
                100                 105                 110

Ile Glu Gly Pro Ser Lys Ala Glu Ile Ser Cys Ile Asp Asn Lys Asp
            115                 120                 125

Gly Thr Cys Thr Val Thr Tyr Leu Pro Thr Leu Pro Gly Asp Tyr Ser
        130                 135                 140

Ile Leu Val Lys Tyr Asn Asp Lys His Ile Pro Gly Ser Pro Phe Thr
145                 150                 155                 160

Ala Lys Ile Thr Asp Asp Ser Arg Arg Cys Ser Gln Val Lys Leu Gly
                165                 170                 175

Ser Ala Ala Asp Phe Leu Leu Asp Ile Ser Glu Thr Asp Leu Ser Ser
                180                 185                 190

Leu Thr Ala Ser Ile Lys Ala Pro Ser Gly Arg Asp Glu Pro Cys Leu
            195                 200                 205

Leu Lys Arg Leu Pro Asn Asn His Ile Gly Ile Ser Phe Ile Pro Arg
        210                 215                 220

Glu Val Gly Glu His Leu Val Ser Ile Lys Lys Asn Gly Asn His Val
225                 230                 235                 240

Ala Asn Ser Pro Val Ser Ile Met Val Val Gln Ser Glu Ile Gly Asp
                245                 250                 255

Ala Arg Arg Ala Lys Val Tyr Gly Arg Gly Leu Ser Glu Gly Arg Thr
                260                 265                 270

Phe Glu Met Ser Asp Phe Ile Val Asp Thr Arg Asp Ala Gly Tyr Gly
            275                 280                 285

Gly Ile Ser Leu Ala Val Glu Gly Pro Ser Lys Val Asp Ile Gln Thr
        290                 295                 300

Glu Asp Leu Glu Asp Gly Thr Cys Lys Val Ser Tyr Phe Pro Thr Val
305                 310                 315                 320

Pro Gly Val Tyr Ile Val Ser Thr Lys Phe Ala Asp Glu His Val Pro
                325                 330                 335

Gly Ser Pro Phe Thr Val Lys Ile Ser Gly Glu Gly Arg Val Lys Glu
                340                 345                 350

Ser Ile Thr Arg Thr Ser Arg Ala Pro Ser Val Ala Thr Val Gly Ser
            355                 360                 365
```

```
Ile Cys Asp Leu Asn Leu Lys Ile Pro Glu Ile Asn Ser Ser Asp Met
    370                 375                 380
Ser Ala His Val Thr Ser Pro Ser Gly Arg Val Thr Glu Ala Glu Ile
385                 390                 395                 400
Val Pro Met Gly Lys Asn Ser His Cys Val Arg Phe Val Pro Gln Glu
                405                 410                 415
Met Gly Val His Thr Val Ser Val Lys Tyr Arg Gly Gln His Val Thr
            420                 425                 430
Gly Ser Pro Phe Gln Phe Thr Val Gly Ala Leu Gly Glu Gly Gly Ala
        435                 440                 445
His Lys Val Arg Ala Gly Gly Pro Gly Leu Glu Arg Gly Glu Ala Gly
    450                 455                 460
Val Pro Ala Glu Phe Ser Ile Trp Thr Arg Glu Ala Gly Ala Gly Gly
465                 470                 475                 480
Leu Ser Ile Ala Val Glu Gly Pro Ser Lys Ala Glu Ile Thr Phe Asp
                485                 490                 495
Asp His Lys Asn Gly Ser Cys Gly Val Ser Tyr Ile Ala Gln Glu Pro
            500                 505                 510
Gly Asn Tyr Glu Val Ser Ile Lys Phe Asn Asp Glu His Ile Pro Glu
        515                 520                 525
Ser Pro Tyr Leu Val Pro Val Ile Ala Pro Ser Asp Asp Ala Arg Arg
    530                 535                 540
Leu Thr Val Met Ser Leu Gln Glu Ser Gly Leu Lys Val Asn Gln Pro
545                 550                 555                 560
Ala Ser Phe Ala Ile Arg Leu Asn Gly Ala Lys Gly Lys Ile Asp Ala
                565                 570                 575
Lys Val His Ser Pro Ser Gly Ala Val Glu Glu Cys His Val Ser Glu
            580                 585                 590
Leu Glu Pro Asp Lys Tyr Ala Val Arg Phe Ile Pro His Glu Asn Gly
        595                 600                 605
Val His Thr Ile Asp Val Lys Phe Asn Gly Ser His Val Val Gly Ser
    610                 615                 620
Pro Phe Lys Val Arg Val Gly Glu Pro Gly Gln Ala Gly Asn Pro Ala
625                 630                 635                 640
Leu Val Ser Ala Tyr Gly Thr Gly Leu Glu Gly Xaa Thr Thr Gly Ile
                645                 650                 655
Gln Ser Glu Phe Phe Ile Asn Thr Thr Arg Ala Gly Pro Gly Thr Leu
            660                 665                 670
Ser Val Thr Ile Glu Gly Pro Ser Lys Val Lys Met Asp Cys Gln Glu
        675                 680                 685
Thr Pro Glu Gly Tyr Lys Val Met Tyr Thr Pro Met Ala Pro Gly Asn
    690                 695                 700
Tyr Leu Ile Ser Val Lys Tyr Gly Gly Pro Asn His Ile Val Gly Ser
705                 710                 715                 720
Pro Phe Lys Ala Lys Val Thr Gly Gln Arg Leu Val Ser Pro Gly Ser
                725                 730                 735
Ala Asn Glu Thr Ser Ser Ile Leu Val Glu Ser Val Thr Arg Ser Ser
            740                 745                 750
Thr Glu Thr Cys Tyr Ser Ala Ile Pro Lys Ala Ser Ser Asp Ala Ser
        755                 760                 765
Lys Val Thr Ser Lys Gly Ala Gly Leu Ser Lys Ala Phe Val Gly Gln
    770                 775                 780
Lys Ser Ser Phe Leu Val Asp Cys Ser Lys Ala Gly Ser Asn Met Leu
```

-continued

```
785              790                 795                800
Leu Ile Gly Val His Gly Pro Thr Thr Pro Cys Glu Glu Val Ser Met
                805                 810                 815

Lys His Val Gly Asn Gln Gln Tyr Asn Val Thr Tyr Val Val Lys Glu
            820                 825                 830

Arg Gly Asp Tyr Val Leu Ala Val Lys Trp Gly Glu Glu His Ile Pro
        835                 840                 845

Gly Ser Pro Phe His Val Thr Val Pro
    850                 855
```

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:3:

```
CGGATCCTCG GATACCGGCT CTCGGTGAAG                                      30
```

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:4:

```
CGGCTCCTCA GAGAGTGGGA CTGTCTGCCT                                      30
```

(2) INFORMATION FOR SEQ ID NO:5:

(i) SEQUENCE CHARACTERISTICS:
        (A) LENGTH: 545 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..534

(xi) SEQUENCE DESCRIPTION: SEQ ID NO:5:

```
AAG GTG AAG ATG GAT TGC CAG GAG TGC CCT GAG GGC TAC CGC GTC ACC        48
Lys Val Lys Met Asp Cys Gln Glu Cys Pro Glu Gly Tyr Arg Val Thr
 1               5                  10                  15

TAT ACC CCC ATG GCA CCT GGC AGC TAC CTC ATC TCC ATC AAG TAC GGC        96
Tyr Thr Pro Met Ala Pro Gly Ser Tyr Leu Ile Ser Ile Lys Tyr Gly
            20                  25                  30

GGC CCC TAC CAC ATT GGG GGC AGC CCC TTC AAG GCC AAA GTC ACA GGC       144
Gly Pro Tyr His Ile Gly Gly Ser Pro Phe Lys Ala Lys Val Thr Gly
        35                  40                  45

CCC CGT CTC GTC AGC AAC CAC AGC CTC CAC GAG ACA TCA TCA GTG TTT       192
Pro Arg Leu Val Ser Asn His Ser Leu His Glu Thr Ser Ser Val Phe
    50                  55                  60

GTA GAC TCT CTG ACC AAG GCC ACC TGT GCC CCC CAG CAT GGG GCC CCG       240
Val Asp Ser Leu Thr Lys Ala Thr Cys Ala Pro Gln His Gly Ala Pro
 65                  70                  75                  80
```

```
GGT CCT GGG CCT GCT GAC GCC AGC AAG GTG GTG GCC AAG GGC CTG GGG         288
Gly Pro Gly Pro Ala Asp Ala Ser Lys Val Val Ala Lys Gly Leu Gly
                85                  90                  95

CTG AGC AAG GCC TAC GTA GGC CAG AAG AGC AGC TTC ACA GTA GAC TGC         336
Leu Ser Lys Ala Tyr Val Gly Gln Lys Ser Ser Phe Thr Val Asp Cys
            100                 105                 110

AGC AAA GCA GGC AAC AAC ATG CTG CTG GTG GGG GTT CAT GGC CCA AGG         384
Ser Lys Ala Gly Asn Asn Met Leu Leu Val Gly Val His Gly Pro Arg
        115                 120                 125

ACC CCC TGC GAG GAG ATC CTG GTG AAG CAC GTG GGC AGC CGG CTC TAC         432
Thr Pro Cys Glu Glu Ile Leu Val Lys His Val Gly Ser Arg Leu Tyr
    130                 135                 140

AGC GTG TCC TAC CTG CTC AAG GAC AAG GGG GAG TAC ACA CTG GTG GTC         480
Ser Val Ser Tyr Leu Leu Lys Asp Lys Gly Glu Tyr Thr Leu Val Val
145                 150                 155                 160

AAA TGG GGG GAC GAG CAC ATC CCA GGC AGN CCC TAC CGN GTT GTG GTG         528
Lys Trp Gly Asp Glu His Ile Pro Gly Xaa Pro Tyr Xaa Val Val Val
                165                 170                 175

CCC TGAGTCTTGG GGCC                                                     545
Pro
```

(2) INFORMATION FOR SEQ ID NO:6:

(i) SEQUENCE CHARACTERISTICS:
        (A) LENGTH: 177 amino acids
        (B) TYPE: amino acid
        (D) TOPOLOGY: Not Relevant (ii) MOLECULE TYPE: protein (xi) SEQUENCE DESCRIPTION: SEQ ID NO:6:

```
Lys Val Lys Met Asp Cys Gln Glu Cys Pro Glu Gly Tyr Arg Val Thr
 1               5                  10                  15

Tyr Thr Pro Met Ala Pro Gly Ser Tyr Leu Ile Ser Ile Lys Tyr Gly
            20                  25                  30

Gly Pro Tyr His Ile Gly Gly Ser Pro Phe Lys Ala Lys Val Thr Gly
        35                  40                  45

Pro Arg Leu Val Ser Asn His Ser Leu His Glu Thr Ser Ser Val Phe
    50                  55                  60

Val Asp Ser Leu Thr Lys Ala Thr Cys Ala Pro Gln His Gly Ala Pro
65                  70                  75                  80

Gly Pro Gly Pro Ala Asp Ala Ser Lys Val Val Ala Lys Gly Leu Gly
                85                  90                  95

Leu Ser Lys Ala Tyr Val Gly Gln Lys Ser Ser Phe Thr Val Asp Cys
            100                 105                 110

Ser Lys Ala Gly Asn Asn Met Leu Leu Val Gly Val His Gly Pro Arg
        115                 120                 125

Thr Pro Cys Glu Glu Ile Leu Val Lys His Val Gly Ser Arg Leu Tyr
    130                 135                 140

Ser Val Ser Tyr Leu Leu Lys Asp Lys Gly Glu Tyr Thr Leu Val Val
145                 150                 155                 160

Lys Trp Gly Asp Glu His Ile Pro Gly Xaa Pro Tyr Xaa Val Val Val
                165                 170                 175

Pro
```

(2) INFORMATION FOR SEQ ID NO:7:

(i) SEQUENCE CHARACTERISTICS:
        (A) LENGTH: 8367 base pairs (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 172..8115

(xi) SEQUENCE DESCRIPTION: SEQ ID NO:7:

```
CGATCCGGGC GCCACCCCGC GGTCATCGGT CACCGGTCGC TCTCAGGAAC AGCAGCGCAA      60

CCTCTGCTCC CTGCCTCGCC TCCCGCGCGC CTAGGTGCCT GCGACTTTAA TTAAAGGGCC     120

GTCCCCTCGC CGAGGCTGCA GCACCGCCCC CCCGGCTTCT CGCGCCTCAA A ATG AGT      177
                                                        Met Ser
                                                          1

AGC TCC CAC TCT CGG GCG GGC CAG AGC GCA GCA GGC GCG GCT CCG GGC       225
Ser Ser His Ser Arg Ala Gly Gln Ser Ala Ala Gly Ala Ala Pro Gly
          5                  10                  15

GGC GGC GTC GAC ACG CGG GAC GCC GAG ATG CCG GCC ACC GAG AAG GAC       273
Gly Gly Val Asp Thr Arg Asp Ala Glu Met Pro Ala Thr Glu Lys Asp
 20                  25                  30

CTG GCG GAG GAC GCG CCG TGG AAG AAG ATC CAG CAG AAC ACT TTC ACG       321
Leu Ala Glu Asp Ala Pro Trp Lys Lys Ile Gln Gln Asn Thr Phe Thr
 35                  40                  45                  50

CGC TGG TGC AAC GAG CAC CTG AAG TGC GTG AGC AAG CGC ATC GCC AAC       369
Arg Trp Cys Asn Glu His Leu Lys Cys Val Ser Lys Arg Ile Ala Asn
                 55                  60                  65

CTG CAG ACG GAC CTG AGC GAC GGG CTG CGG CTT ATC GCG CTG TTG GAG       417
Leu Gln Thr Asp Leu Ser Asp Gly Leu Arg Leu Ile Ala Leu Leu Glu
                 70                  75                  80

GTG CTC AGC CAG AAG AAG ATG CAC CGC AAG CAC AAC CAG CGG CCC ACT       465
Val Leu Ser Gln Lys Lys Met His Arg Lys His Asn Gln Arg Pro Thr
             85                  90                  95

TTC CGC CAA ATG CAG CTT GAG AAC GTG TCG GTG GCG CTC GAG TTC CTG       513
Phe Arg Gln Met Gln Leu Glu Asn Val Ser Val Ala Leu Glu Phe Leu
100                 105                 110

GAC CGC GAG AGC ATC AAA CTG GTG TCC ATC GAC AGC AAG GCC ATC GTG       561
Asp Arg Glu Ser Ile Lys Leu Val Ser Ile Asp Ser Lys Ala Ile Val
115                 120                 125                 130

GAC GGG AAC CTG AAG CTG ATC CTG GGC CTC ATC TGG ACC CTG ATC CTG       609
Asp Gly Asn Leu Lys Leu Ile Leu Gly Leu Ile Trp Thr Leu Ile Leu
                135                 140                 145

CAC TAC TCC ATC TCC ATG CCC ATG TGG GAC GAG GAG GAG GAT GAG GAG       657
His Tyr Ser Ile Ser Met Pro Met Trp Asp Glu Glu Glu Asp Glu Glu
                150                 155                 160

GCC AAG AAG CAG ACC CCC AAG CAG AGG CTC CTG GGC TGG ATC CAG AAC       705
Ala Lys Lys Gln Thr Pro Lys Gln Arg Leu Leu Gly Trp Ile Gln Asn
            165                 170                 175

AAG CTG CCG CAG CTG CCC ATC ACC AAC TTC AGC CGG GAC TGG CAG AGC       753
Lys Leu Pro Gln Leu Pro Ile Thr Asn Phe Ser Arg Asp Trp Gln Ser
180                 185                 190

GGC CGG GCC CTG GGC GCC CTG GTG GAC AGC TGT GCC CCG GGC CTG TGT       801
Gly Arg Ala Leu Gly Ala Leu Val Asp Ser Cys Ala Pro Gly Leu Cys
195                 200                 205                 210

CCT GAC TGG GAC TCT TGG GAC GCC AGC AAG CCC GTT ACC AAT GCG CGA       849
Pro Asp Trp Asp Ser Trp Asp Ala Ser Lys Pro Val Thr Asn Ala Arg
                215                 220                 225

GAG GCC ATG CAG CAG GCG GAT GAC TGG CTG GGC ATC CCC CAG GTG ATC       897
Glu Ala Met Gln Gln Ala Asp Asp Trp Leu Gly Ile Pro Gln Val Ile
                230                 235                 240
```

```
ACC CCC GAG GAG ATT GTG GAC CCC AAC GTG GAC GAG CAC TCT GTC ATG        945
Thr Pro Glu Glu Ile Val Asp Pro Asn Val Asp Glu His Ser Val Met
        245                 250                 255

ACC TAC CTG TCC CAG TTC CCC AAG GCC AAG CTG AAG CCA GGG GCT CCC        993
Thr Tyr Leu Ser Gln Phe Pro Lys Ala Lys Leu Lys Pro Gly Ala Pro
    260                 265                 270

TTG CGC CCC AAA CTG AAC CCG AAG AAA GCC CGT GCC TAC GGG CCA GGC       1041
Leu Arg Pro Lys Leu Asn Pro Lys Lys Ala Arg Ala Tyr Gly Pro Gly
275                 280                 285                 290

ATC GAG CCC ACA GGC AAC ATG GTG AAG AAG CGG GCA GAG TTC ACT GTG       1089
Ile Glu Pro Thr Gly Asn Met Val Lys Lys Arg Ala Glu Phe Thr Val
                295                 300                 305

GAG ACC AGA AGT GCT GGC CAG GGA GAG GTG CTG GTG TAC GTG GAG GAC       1137
Glu Thr Arg Ser Ala Gly Gln Gly Glu Val Leu Val Tyr Val Glu Asp
            310                 315                 320

CCG GCC GGA CAC CAG GAG GAG GCA AAA GTG ACC GCC AAT AAC GAC AAG       1185
Pro Ala Gly His Gln Glu Glu Ala Lys Val Thr Ala Asn Asn Asp Lys
        325                 330                 335

AAC CGC ACC TTC TCC GTC TGG TAC GTC CCC GAG GTG ACG GGG ACT CAT       1233
Asn Arg Thr Phe Ser Val Trp Tyr Val Pro Glu Val Thr Gly Thr His
    340                 345                 350

AAG GTT ACT GTG CTC TTT GCT GGC CAG CAC ATC GCC AAG AGC CCC TTC       1281
Lys Val Thr Val Leu Phe Ala Gly Gln His Ile Ala Lys Ser Pro Phe
355                 360                 365                 370

GAG GTG TAC GTG GAT AAG TCA CAG GGT GAC GCC AGC AAA GTG ACA GCC       1329
Glu Val Tyr Val Asp Lys Ser Gln Gly Asp Ala Ser Lys Val Thr Ala
                375                 380                 385

CAA GGT CCC GGC CTG GAG CCC AGT GGC AAC ATC GCC AAC AAG ACC ACC       1377
Gln Gly Pro Gly Leu Glu Pro Ser Gly Asn Ile Ala Asn Lys Thr Thr
            390                 395                 400

TAC TTT GAG ATC TTT ACG GCA GGA GCT GGC ACG GGC GAG GTC GAG GTT       1425
Tyr Phe Glu Ile Phe Thr Ala Gly Ala Gly Thr Gly Glu Val Glu Val
        405                 410                 415

GTG ATC CAG GAC CCC ATG GGA CAG AAG GGC ACG GTA GAG CCT CAG CTG       1473
Val Ile Gln Asp Pro Met Gly Gln Lys Gly Thr Val Glu Pro Gln Leu
    420                 425                 430

GAG GCC CGG GGC GAC AGC ACA TAC CGC TGC AGC TAC CAG CCC ACC ATG       1521
Glu Ala Arg Gly Asp Ser Thr Tyr Arg Cys Ser Tyr Gln Pro Thr Met
435                 440                 445                 450

GAG GGC GTC CAC ACC GTG CAC GTC ACG TTT GCC GGC GTG CCC ATC CCT       1569
Glu Gly Val His Thr Val His Val Thr Phe Ala Gly Val Pro Ile Pro
                455                 460                 465

CGC AGC CCC TAC ACT GTC ACT GTT GGC CAA GCC TGT AAC CCG AGT GCC       1617
Arg Ser Pro Tyr Thr Val Thr Val Gly Gln Ala Cys Asn Pro Ser Ala
            470                 475                 480

TGC CGG GCG GTT GGC CGG GGC CTC CAG CCC AAG GGT GTG CGG GTG AAG       1665
Cys Arg Ala Val Gly Arg Gly Leu Gln Pro Lys Gly Val Arg Val Lys
        485                 490                 495

GAG ACA GCT GAC TTC AAG GTG TAC ACA AAG GGC GCT GGC AGT GGG GAG       1713
Glu Thr Ala Asp Phe Lys Val Tyr Thr Lys Gly Ala Gly Ser Gly Glu
    500                 505                 510

CTG AAG GTC ACC GTG AAG GGC CCC AAG GGA GAG GAG CGC GTG AAG CAG       1761
Leu Lys Val Thr Val Lys Gly Pro Lys Gly Glu Glu Arg Val Lys Gln
515                 520                 525                 530

AAG GAC CTG GGG GAT GGC GTG TAT GGC TTC GAG TAT TAC CCC ATG GTC       1809
Lys Asp Leu Gly Asp Gly Val Tyr Gly Phe Glu Tyr Tyr Pro Met Val
                535                 540                 545

CCT GGA ACC TAT ATC GTC ACC ATC ACG TGG GGT GGT CAG AAC ATC GGG       1857
Pro Gly Thr Tyr Ile Val Thr Ile Thr Trp Gly Gly Gln Asn Ile Gly
            550                 555                 560
```

```
CGC AGT CCC TTC GAA GTG AAG GTG GGC ACC GAG TGT GGC AAT CAG AAG    1905
Arg Ser Pro Phe Glu Val Lys Val Gly Thr Glu Cys Gly Asn Gln Lys
        565                 570                 575

GTA CGG GCC TGG GGC CCT GGG CTG GAG GGC GGC GTC GTT GGC AAG TCA    1953
Val Arg Ala Trp Gly Pro Gly Leu Glu Gly Gly Val Val Gly Lys Ser
580                 585                 590

GCA GAC TTT GTG GTG GAG GCT ATC GGG GAC GAC GTG GGC ACG CTG GGC    2001
Ala Asp Phe Val Val Glu Ala Ile Gly Asp Asp Val Gly Thr Leu Gly
595                 600                 605                 610

TTC TCG GTG GAA GGG CCA TCG CAG GCT AAG ATC GAA TGT GAC GAC AAG    2049
Phe Ser Val Glu Gly Pro Ser Gln Ala Lys Ile Glu Cys Asp Asp Lys
        615                 620                 625

GGC GAC GGC TCC TGT GAT GTG CGC TAC TGG CCG CAG GAG GCT GGC GAG    2097
Gly Asp Gly Ser Cys Asp Val Arg Tyr Trp Pro Gln Glu Ala Gly Glu
                630                 635                 640

TAT GCC GTT CAC GTG CTG TGC AAC AGC GAA GAC ATC CGC CTC AGC CCC    2145
Tyr Ala Val His Val Leu Cys Asn Ser Glu Asp Ile Arg Leu Ser Pro
            645                 650                 655

TTC ATG GCT GAC ATC CGT GAC GCG CCC CAG GAC TTC CAC CCA GAC AGG    2193
Phe Met Ala Asp Ile Arg Asp Ala Pro Gln Asp Phe His Pro Asp Arg
660                 665                 670

GTG AAG GCA CGT GGG CCT GGA TTG GAG AAG ACA GGT GTG GCC GTC AAC    2241
Val Lys Ala Arg Gly Pro Gly Leu Glu Lys Thr Gly Val Ala Val Asn
675                 680                 685                 690

AAG CCA GCA GAG TTC ACA GTG GAT GCC AAG CAC GGT GGC AAG GCC CCA    2289
Lys Pro Ala Glu Phe Thr Val Asp Ala Lys His Gly Gly Lys Ala Pro
                695                 700                 705

CTT CGG GTC CAA GTC CAG GAC AAT GAA GGC TGC CCT GTG GAG GCG TTG    2337
Leu Arg Val Gln Val Gln Asp Asn Glu Gly Cys Pro Val Glu Ala Leu
            710                 715                 720

GTC AAG GAC AAC GGC AAT GGC ACT TAC AGC TGC TCC TAC GTG CCC AGG    2385
Val Lys Asp Asn Gly Asn Gly Thr Tyr Ser Cys Ser Tyr Val Pro Arg
        725                 730                 735

AAG CCG GTG AAG CAC ACA GCC ATG GTG TCC TGG GGA GGC GTC AGC ATC    2433
Lys Pro Val Lys His Thr Ala Met Val Ser Trp Gly Gly Val Ser Ile
    740                 745                 750

CCC AAC AGC CCC TTC AGG GTG AAT GTG GGA GCT GGC AGC CAC CCC AAC    2481
Pro Asn Ser Pro Phe Arg Val Asn Val Gly Ala Gly Ser His Pro Asn
755                 760                 765                 770

AAG GTC AAA GTA TAC GGC CCC GGA GTA GCC AAG ACA GGG CTC AAG GCC    2529
Lys Val Lys Val Tyr Gly Pro Gly Val Ala Lys Thr Gly Leu Lys Ala
                775                 780                 785

CAC GAG CCC ACC TAC TTC ACT GTG GAC TGC GCC GAG GCT GGC CAG GGG    2577
His Glu Pro Thr Tyr Phe Thr Val Asp Cys Ala Glu Ala Gly Gln Gly
            790                 795                 800

GAC GTC AGC ATC GGC ATC AAG TGT GCC CCT GGA GTG GTA GGC CCC GCC    2625
Asp Val Ser Ile Gly Ile Lys Cys Ala Pro Gly Val Val Gly Pro Ala
        805                 810                 815

GAA GCT GAC ATC GAC TTC GAC ATC ATC CGC AAT GAC AAT GAC ACC TTC    2673
Glu Ala Asp Ile Asp Phe Asp Ile Ile Arg Asn Asp Asn Asp Thr Phe
820                 825                 830

ACG GTC AAG TAC ACG CCC CGG GGG GCT GGC AGC TAC ACC ATT ATG GTC    2721
Thr Val Lys Tyr Thr Pro Arg Gly Ala Gly Ser Tyr Thr Ile Met Val
835                 840                 845                 850

CTC TTT GCT GAC CAG GCC ACG CCC ACC AGC CCC ATC CGA GTC AAG GTG    2769
Leu Phe Ala Asp Gln Ala Thr Pro Thr Ser Pro Ile Arg Val Lys Val
                855                 860                 865

GAG CCC TCT CAT GAC GCC AGT AAG GTG AAG GCC GAG GGC CCT GGC CTC    2817
Glu Pro Ser His Asp Ala Ser Lys Val Lys Ala Glu Gly Pro Gly Leu
            870                 875                 880
```

| | | |
|---|---|---|
| AGT CGC ACT GGT GTC GAG CTT GGC AAG CCC ACC CAC TTC ACA GTA AAT<br>Ser Arg Thr Gly Val Glu Leu Gly Lys Pro Thr His Phe Thr Val Asn<br>          885                   890                   895 | 2865 |
| GCC AAA GCT GCT GGC AAA GGC AAG CTG GAC GTC CAG TTC TCA GGA CTC<br>Ala Lys Ala Ala Gly Lys Gly Lys Leu Asp Val Gln Phe Ser Gly Leu<br>900                   905                   910 | 2913 |
| ACC AAG GGG GAT GCA GTG CGA GAT GTG GAC ATC ATC GAC CAC CAT GAC<br>Thr Lys Gly Asp Ala Val Arg Asp Val Asp Ile Ile Asp His His Asp<br>915                   920                   925                   930 | 2961 |
| AAC ACC TAC ACA GTC AAG TAC ACG CCT GTC CAG CAG GGT CCA GTA GGC<br>Asn Thr Tyr Thr Val Lys Tyr Thr Pro Val Gln Gln Gly Pro Val Gly<br>                   935                   940                   945 | 3009 |
| GTC AAT GTC ACT TAT GGA GGG GAT CCC ATC CCT AAG AGC CCT TTC TCA<br>Val Asn Val Thr Tyr Gly Gly Asp Pro Ile Pro Lys Ser Pro Phe Ser<br>                  950                   955                   960 | 3057 |
| GTG GCA GTA TCT CCA AGC CTG GAC CTC AGC AAG ATC AAG GTG TCT GGC<br>Val Ala Val Ser Pro Ser Leu Asp Leu Ser Lys Ile Lys Val Ser Gly<br>         965                   970                   975 | 3105 |
| CTG GGA GAG AAG GTG GAC GTT GGC AAA GAC CAG GAG TTC ACA GTC AAA<br>Leu Gly Glu Lys Val Asp Val Gly Lys Asp Gln Glu Phe Thr Val Lys<br>               980                   985                   990 | 3153 |
| TCA AAG GGT GCT GGT GGT CAA GGC AAA GTG GCA TCC AAG ATT GTG GGC<br>Ser Lys Gly Ala Gly Gly Gln Gly Lys Val Ala Ser Lys Ile Val Gly<br>995                   1000                 1005                 1010 | 3201 |
| CCC TCG GGT GCA GCG GTG CCC TGC AAG GTG GAG CCA GGC CTG GGG GCT<br>Pro Ser Gly Ala Ala Val Pro Cys Lys Val Glu Pro Gly Leu Gly Ala<br>                   1015                 1020                 1025 | 3249 |
| GAC AAC AGT GTG GTG CGC TTC CTG CCC CGT GAG GAA GGG CCC TAT GAG<br>Asp Asn Ser Val Val Arg Phe Leu Pro Arg Glu Glu Gly Pro Tyr Glu<br>                   1030                 1035                 1040 | 3297 |
| GTG GAG GTG ACC TAT GAC GGC GTG CCC GTG CCT GGC AGC CCC TTT CCT<br>Val Glu Val Thr Tyr Asp Gly Val Pro Val Pro Gly Ser Pro Phe Pro<br>                   1045                 1050                 1055 | 3345 |
| CTG GAA GCT GTG GCC CCC ACC AAG CCT AGC AAG GTG AAG GCG TTT GGG<br>Leu Glu Ala Val Ala Pro Thr Lys Pro Ser Lys Val Lys Ala Phe Gly<br>                   1060                 1065                 1070 | 3393 |
| CCG GGG CTG CAG GGA GGC AGT GCG GGC TCC CCC GCC CGC TTC ACC ATC<br>Pro Gly Leu Gln Gly Gly Ser Ala Gly Ser Pro Ala Arg Phe Thr Ile<br>1075                 1080                 1085                 1090 | 3441 |
| GAC ACC AAG GGC GCC GGC ACA GGT GGC CTG GGC CTG ACG GTG GAG GGC<br>Asp Thr Lys Gly Ala Gly Thr Gly Gly Leu Gly Leu Thr Val Glu Gly<br>                   1095                 1100                 1105 | 3489 |
| CCC TGT GAG GCG CAG CTC GAG TGC TTG GAC AAT GGG GAT GGC ACA TGT<br>Pro Cys Glu Ala Gln Leu Glu Cys Leu Asp Asn Gly Asp Gly Thr Cys<br>                   1110                 1115                 1120 | 3537 |
| TCC GTG TCC TAC GTG CCC ACC GAG CCC GGG GAC TAC AAC ATC AAC ATC<br>Ser Val Ser Tyr Val Pro Thr Glu Pro Gly Asp Tyr Asn Ile Asn Ile<br>                   1125                 1130                 1135 | 3585 |
| CTC TTC GCT GAC ACC CAC ATC CCT GGC TCC CCA TTC AAG GCC CAC GTG<br>Leu Phe Ala Asp Thr His Ile Pro Gly Ser Pro Phe Lys Ala His Val<br>         1140                   1145                 1150 | 3633 |
| GTT CCC TGC TTT GAC GCA TCC AAA GTC AAG TGC TCA GGC CCC GGG CTG<br>Val Pro Cys Phe Asp Ala Ser Lys Val Lys Cys Ser Gly Pro Gly Leu<br>1155                 1160                 1165                 1170 | 3681 |
| GAG CGG GCC ACC GCT GGG GAG GTG GGC CAA TTC CAA GTG GAC TGC TCG<br>Glu Arg Ala Thr Ala Gly Glu Val Gly Gln Phe Gln Val Asp Cys Ser<br>                   1175                 1180                 1185 | 3729 |
| AGC GCG GGC AGC GCG GAG CTG ACC ATT GAG ATC TGC TCG GAG GCG GGG<br>Ser Ala Gly Ser Ala Glu Leu Thr Ile Glu Ile Cys Ser Glu Ala Gly<br>                   1190                 1195                 1200 | 3777 |

-continued

| | |
|---|---|
| CTT CCG GCC GAG GTG TAC ATC CAG GAC CAC GGT GAT GGC ACG CAC ACC<br>Leu Pro Ala Glu Val Tyr Ile Gln Asp His Gly Asp Gly Thr His Thr<br>    1205                      1210                      1215 | 3825 |
| ATT ACC TAC ATT CCC CTC TGC CCC GGG GCC TAC ACC GTC ACC ATC AAG<br>Ile Thr Tyr Ile Pro Leu Cys Pro Gly Ala Tyr Thr Val Thr Ile Lys<br>1220                      1225                      1230 | 3873 |
| TAC GGC GGC CAG CCC GTG CCC AAC TTC CCC AGC AAG CTG CAG GTG GAA<br>Tyr Gly Gly Gln Pro Val Pro Asn Phe Pro Ser Lys Leu Gln Val Glu<br>1235                      1240                      1245                      1250 | 3921 |
| CCT GCG GTG GAC ACT TCC GGT GTC CAG TGC TAT GGG CCT GGT ATT GAG<br>Pro Ala Val Asp Thr Ser Gly Val Gln Cys Tyr Gly Pro Gly Ile Glu<br>                      1255                      1260                      1265 | 3969 |
| GGC CAG GGT GTC TTC CGT GAG GCC ACC ACT GAG TTC AGT GTG GAC GCC<br>Gly Gln Gly Val Phe Arg Glu Ala Thr Thr Glu Phe Ser Val Asp Ala<br>1270                      1275                      1280 | 4017 |
| CGG GCT CTG ACA CAG ACC GGA GGG CCG CAC GTC AAG GCC CGT GTG GCC<br>Arg Ala Leu Thr Gln Thr Gly Gly Pro His Val Lys Ala Arg Val Ala<br>                      1285                      1290                      1295 | 4065 |
| AAC CCC TCA GGC AAC CTG ACG GAG ACC TAC GTT CAG GAC CGT GGC GAT<br>Asn Pro Ser Gly Asn Leu Thr Glu Thr Tyr Val Gln Asp Arg Gly Asp<br>1300                      1305                      1310 | 4113 |
| GGC ATG TAC AAA GTG GAG TAC ACG CCT TAC GAG GAG GGA CTG CAC TCC<br>Gly Met Tyr Lys Val Glu Tyr Thr Pro Tyr Glu Glu Gly Leu His Ser<br>1315                      1320                      1325                      1330 | 4161 |
| GTG GAC GTG ACC TAT GAC GGC AGT CCC GTG CCC AGC AGC CCC TTC CAG<br>Val Asp Val Thr Tyr Asp Gly Ser Pro Val Pro Ser Ser Pro Phe Gln<br>                      1335                      1340                      1345 | 4209 |
| GTG CCC GTG ACC GAG GGC TGC GAC CCC TCC CGG GTG CGT GTC CAC GGG<br>Val Pro Val Thr Glu Gly Cys Asp Pro Ser Arg Val Arg Val His Gly<br>1350                      1355                      1360 | 4257 |
| CCA GGC ATC CAA AGT GGC ACC ACC AAC AAG CCC AAC AAG TTC ACT GTG<br>Pro Gly Ile Gln Ser Gly Thr Thr Asn Lys Pro Asn Lys Phe Thr Val<br>                      1365                      1370                      1375 | 4305 |
| GAG ACC AGG GGA GCT GGC ACG GGC GGC CTG GGC CTG GCT GTA GAG GGC<br>Glu Thr Arg Gly Ala Gly Thr Gly Gly Leu Gly Leu Ala Val Glu Gly<br>1380                      1385                      1390 | 4353 |
| CCC TCC GAG GCC AAG ATG TCC TGC ATG GAT AAC AAG GAC GGC AGC TGC<br>Pro Ser Glu Ala Lys Met Ser Cys Met Asp Asn Lys Asp Gly Ser Cys<br>1395                      1400                      1405                      1410 | 4401 |
| TCG GTC GAG TAC ATC CCT TAT GAG GCT GGC ACC TAC AGC CTC AAC GTC<br>Ser Val Glu Tyr Ile Pro Tyr Glu Ala Gly Thr Tyr Ser Leu Asn Val<br>                      1415                      1420                      1425 | 4449 |
| ACC TAT GGT GGC CAT CAA GTG CCA GGC AGT CCT TTC AAG GTC CCT GTG<br>Thr Tyr Gly Gly His Gln Val Pro Gly Ser Pro Phe Lys Val Pro Val<br>1430                      1435                      1440 | 4497 |
| CAT GAT GTG ACA GAT GCG TCC AAG GTC AAG TGC TCT GGG CCC GGC CTG<br>His Asp Val Thr Asp Ala Ser Lys Val Lys Cys Ser Gly Pro Gly Leu<br>                      1445                      1450                      1455 | 4545 |
| AGC CCA GGC ATG GTT CGT GCC AAC CTC CCT CAG TCC TTC CAG GTG GAC<br>Ser Pro Gly Met Val Arg Ala Asn Leu Pro Gln Ser Phe Gln Val Asp<br>1460                      1465                      1470 | 4593 |
| ACA AGC AAG GCT GGT GTG GCC CCA TTG CAG GTC AAA GTG CAA GGG CCC<br>Thr Ser Lys Ala Gly Val Ala Pro Leu Gln Val Lys Val Gln Gly Pro<br>1475                      1480                      1485                      1490 | 4641 |
| AAA GGC CTG GTG GAG CCA GTG GAC GTG GTA GAC AAC GCT GAT GGC ACC<br>Lys Gly Leu Val Glu Pro Val Asp Val Val Asp Asn Ala Asp Gly Thr<br>                      1495                      1500                      1505 | 4689 |
| CAG ACC GTC AAT TAT GTG CCC AGC CGA GAA GGG CCC TAC AGC ATC TCA<br>Gln Thr Val Asn Tyr Val Pro Ser Arg Glu Gly Pro Tyr Ser Ile Ser<br>1510                      1515                      1520 | 4737 |

```
GTA CTG TAT GGA GAT GAA GAG GTA CCC CGG AGC CCC TTC AAG GTC AAG         4785
Val Leu Tyr Gly Asp Glu Glu Val Pro Arg Ser Pro Phe Lys Val Lys
    1525                1530                1535

GTG CTG CCT ACT CAT GAT GCC AGC AAG GTG AAG GCC AGT GGC CCC GGG         4833
Val Leu Pro Thr His Asp Ala Ser Lys Val Lys Ala Ser Gly Pro Gly
1540                1545                1550

CTC AAC ACC ACT GGC GTG CCT GCC AGC CTG CCC GTG GAG TTC ACC ATC         4881
Leu Asn Thr Thr Gly Val Pro Ala Ser Leu Pro Val Glu Phe Thr Ile
1555                1560                1565                1570

GAT GCA AAG GAC GCC GGG GAG GGC CTG CTG GCT GTC CAG ATC ACG GAT         4929
Asp Ala Lys Asp Ala Gly Glu Gly Leu Leu Ala Val Gln Ile Thr Asp
            1575                1580                1585

CCC GAA GGC AAG CCG AAG AAG ACA CAC ATC CAA GAC AAC CAT GAC GGC         4977
Pro Glu Gly Lys Pro Lys Lys Thr His Ile Gln Asp Asn His Asp Gly
        1590                1595                1600

ACG TAT ACA GTG GCC TAC GTG CCA GAC GTG ACA GGT CGC TAC ACC ATC         5025
Thr Tyr Thr Val Ala Tyr Val Pro Asp Val Thr Gly Arg Tyr Thr Ile
    1605                1610                1615

CTC ATC AAG TAC GGT GGT GAC GAG ATC CCC TTC TCC CCG TAC CGC GTG         5073
Leu Ile Lys Tyr Gly Gly Asp Glu Ile Pro Phe Ser Pro Tyr Arg Val
1620                1625                1630

CGT GCC GTG CCC ACC GGG GAC GCC AGC AAG TGC ACT GTC ACA GTG TCA         5121
Arg Ala Val Pro Thr Gly Asp Ala Ser Lys Cys Thr Val Thr Val Ser
1635                1640                1645                1650

ATC GGA GGT CAC GGG CTA GGT GCT GGC ATC GGC CCC ACC ATT CAG ATT         5169
Ile Gly Gly His Gly Leu Gly Ala Gly Ile Gly Pro Thr Ile Gln Ile
            1655                1660                1665

GGG GAG GAG ACG GTG ATC ACT GTG GAC ACT AAG GCG GCA GGC AAA GGC         5217
Gly Glu Glu Thr Val Ile Thr Val Asp Thr Lys Ala Ala Gly Lys Gly
        1670                1675                1680

AAA GTG ACG TGC ACC GTG TGC ACG CCT GAT GGC TCA GAG GTG GAT GTG         5265
Lys Val Thr Cys Thr Val Cys Thr Pro Asp Gly Ser Glu Val Asp Val
    1685                1690                1695

GAC GTG GTG GAG AAT GAG GAC GGC ACT TTC GAC ATC TTC TAC ACG GCC         5313
Asp Val Val Glu Asn Glu Asp Gly Thr Phe Asp Ile Phe Tyr Thr Ala
1700                1705                1710

CCC CAG CCG GGC AAA TAC GTC ATC TGT GTG CGC TTT GGT GGC GAG CAC         5361
Pro Gln Pro Gly Lys Tyr Val Ile Cys Val Arg Phe Gly Gly Glu His
1715                1720                1725                1730

GTG CCC AAC AGC CCC TTC CAA GTG ACG GCT CTG GCT GGG GAC CAG CCC         5409
Val Pro Asn Ser Pro Phe Gln Val Thr Ala Leu Ala Gly Asp Gln Pro
            1735                1740                1745

TCG GTG CAG CCC CCT CTA CGG TCT CAG CAG CTG GCC CCA CAG TAC ACC         5457
Ser Val Gln Pro Pro Leu Arg Ser Gln Gln Leu Ala Pro Gln Tyr Thr
        1750                1755                1760

TAC GCC CAG GGC GGC CAG CAG ACT TGG GCC CCG GAG AGG CCC CTG GTG         5505
Tyr Ala Gln Gly Gly Gln Gln Thr Trp Ala Pro Glu Arg Pro Leu Val
    1765                1770                1775

GGT GTC AAT GGG CTG GAT GTG ACC AGC CTG AGG CCC TTT GAC CTT GTC         5553
Gly Val Asn Gly Leu Asp Val Thr Ser Leu Arg Pro Phe Asp Leu Val
1780                1785                1790

ATC CCC TTC ACC ATC AAG AAG GGC GAG ATC ACA GGG GAG GTT CGG ATG         5601
Ile Pro Phe Thr Ile Lys Lys Gly Glu Ile Thr Gly Glu Val Arg Met
1795                1800                1805                1810

CCC TCA GGC AAG GTG GCG CAG CCC ACC ATC ACT GAC AAC AAA GAC GGC         5649
Pro Ser Gly Lys Val Ala Gln Pro Thr Ile Thr Asp Asn Lys Asp Gly
            1815                1820                1825

ACC GTG ACC GTG CGG TAT GCA CCC AGC GAG GCT GGC CTG CAC GAG ATG         5697
Thr Val Thr Val Arg Tyr Ala Pro Ser Glu Ala Gly Leu His Glu Met
        1830                1835                1840
```

```
GAC ATC CGC TAT GAC AAC ATG CAC ATC CCA GGA AGC CCC TTG CAG TTC      5745
Asp Ile Arg Tyr Asp Asn Met His Ile Pro Gly Ser Pro Leu Gln Phe
            1845                1850                1855

TAT GTG GAT TAC GTC AAC TGT GGC CAT GTC ACT GCC TAT GGG CCT GGC      5793
Tyr Val Asp Tyr Val Asn Cys Gly His Val Thr Ala Tyr Gly Pro Gly
        1860                1865                1870

CTC ACC CAT GGA GTA GTG AAC AAG CCT GCC ACC TTC ACC GTC AAC ACC      5841
Leu Thr His Gly Val Val Asn Lys Pro Ala Thr Phe Thr Val Asn Thr
1875                1880                1885                1890

AAG GAT GCA GGA GAG GGG GGC CTG TCT CTG GCC ATT GAG GGC CCG TCC      5889
Lys Asp Ala Gly Glu Gly Gly Leu Ser Leu Ala Ile Glu Gly Pro Ser
                1895                1900                1905

AAA GCA GAA ATC AGC TGC ACT GAC AAC CAG GAT GGG ACA TGC AGC GTG      5937
Lys Ala Glu Ile Ser Cys Thr Asp Asn Gln Asp Gly Thr Cys Ser Val
            1910                1915                1920

TCC TAC CTG CCT GTG CTG CCG GGG GAC TAC AGC ATT CTA GTC AAG TAC      5985
Ser Tyr Leu Pro Val Leu Pro Gly Asp Tyr Ser Ile Leu Val Lys Tyr
        1925                1930                1935

AAT GAA CAG CAC GTC CCA GGC AGC CCC TTC ACT GCT CGG GTC ACA GGT      6033
Asn Glu Gln His Val Pro Gly Ser Pro Phe Thr Ala Arg Val Thr Gly
1940                1945                1950

GAC GAC TCC ATG CGT ATG TCC CAC CTA AAG GTC GGC TCT GCT GCC GAC      6081
Asp Asp Ser Met Arg Met Ser His Leu Lys Val Gly Ser Ala Ala Asp
1955                1960                1965                1970

ATC CCC ATC AAC ATC TCA GAG ACG GAT CTC AGC CTG CTG ACG GCC ACT      6129
Ile Pro Ile Asn Ile Ser Glu Thr Asp Leu Ser Leu Leu Thr Ala Thr
                1975                1980                1985

GTG GTC CCG CCC TCG GGC CGG GAG GAG CCC TGT TTG CTG AAG CGG CTG      6177
Val Val Pro Pro Ser Gly Arg Glu Glu Pro Cys Leu Leu Lys Arg Leu
            1990                1995                2000

CGT AAT GGC CAC GTG GGG ATT TCA TTC GTG CCC AAG GAG ACG GGG GAG      6225
Arg Asn Gly His Val Gly Ile Ser Phe Val Pro Lys Glu Thr Gly Glu
        2005                2010                2015

CAC CTG GTG CAT GTG AAG AAA AAT GGC CAG CAC GTG GCC AGC AGC CCC      6273
His Leu Val His Val Lys Lys Asn Gly Gln His Val Ala Ser Ser Pro
2020                2025                2030

ATC CCG GTG GTG ATC AGC CAG TCG GAA ATT GGG GAT GCC AGT CGT GTT      6321
Ile Pro Val Val Ile Ser Gln Ser Glu Ile Gly Asp Ala Ser Arg Val
2035                2040                2045                2050

CGG GTC TCT GGT CAG GGC CTT CAC GAA GGC CAC ACC TTT GAG CCT GCA      6369
Arg Val Ser Gly Gln Gly Leu His Glu Gly His Thr Phe Glu Pro Ala
                2055                2060                2065

GAG TTT ATC ATT GAT ACC CGC GAT GCA GGC TAT GGT GGG CTC AGC CTG      6417
Glu Phe Ile Ile Asp Thr Arg Asp Ala Gly Tyr Gly Gly Leu Ser Leu
            2070                2075                2080

TCC ATT GAG GGC CCC AGC AAG GTG GAC ATC AAC ACA GAG GAC CTG GAG      6465
Ser Ile Glu Gly Pro Ser Lys Val Asp Ile Asn Thr Glu Asp Leu Glu
        2085                2090                2095

GAC GGG ACG TGC AGG GTC ACC TAC TGC CCC ACA GAG CCA GGC AAC TAC      6513
Asp Gly Thr Cys Arg Val Thr Tyr Cys Pro Thr Glu Pro Gly Asn Tyr
2100                2105                2110

ATC ATC AAC ATC AAG TTT GCC GAC CAG CAC GTG CCT GGC AGC CCC TTC      6561
Ile Ile Asn Ile Lys Phe Ala Asp Gln His Val Pro Gly Ser Pro Phe
2115                2120                2125                2130

TCT GTG AAG GTG ACA GGC GAG GGC CGG GTG AAA GAG AGC ATC ACC CGC      6609
Ser Val Lys Val Thr Gly Glu Gly Arg Val Lys Glu Ser Ile Thr Arg
                2135                2140                2145

AGG CGT CGG GCT CCT TCA GTG GCC AAC GTT GGT AGT CAT TGT GAC CTC      6657
Arg Arg Arg Ala Pro Ser Val Ala Asn Val Gly Ser His Cys Asp Leu
            2150                2155                2160
```

```
AGC CTG AAA ATC CCT GAA ATT AGC ATC CAG GAT ATG ACA GCC CAG GTG        6705
Ser Leu Lys Ile Pro Glu Ile Ser Ile Gln Asp Met Thr Ala Gln Val
        2165                2170                2175

ACC AGC CCA TCG GGC AAG ACC CAT GAG GCC GAG ATC GTG GAA GGG GAG        6753
Thr Ser Pro Ser Gly Lys Thr His Glu Ala Glu Ile Val Glu Gly Glu
        2180                2185                2190

AAC CAC ACC TAC TGC ATC CGC TTT GTT CCC GCT GAG ATG GGC ACA CAC        6801
Asn His Thr Tyr Cys Ile Arg Phe Val Pro Ala Glu Met Gly Thr His
2195                2200                2205                2210

ACA GTC AGC GTC AAG TAC AAG GGC CAG CAC GTG CCT GGG AGC CCC TTC        6849
Thr Val Ser Val Lys Tyr Lys Gly Gln His Val Pro Gly Ser Pro Phe
                2215                2220                2225

CAG TTC ACC GTG GGG CCC CTA GGG GAA GGG GGA GCC CAC AAG GTC CGA        6897
Gln Phe Thr Val Gly Pro Leu Gly Glu Gly Gly Ala His Lys Val Arg
        2230                2235                2240

GCT GGG GGC CCT GGC CTG GAG AGA GCT GAA GCT GGA GTG CCA GCC GAA        6945
Ala Gly Gly Pro Gly Leu Glu Arg Ala Glu Ala Gly Val Pro Ala Glu
        2245                2250                2255

TTC AGT ATC TGG ACC CGG GAA GCT GGT GCT GGA GGC CTG GCC ATT GCT        6993
Phe Ser Ile Trp Thr Arg Glu Ala Gly Ala Gly Gly Leu Ala Ile Ala
        2260                2265                2270

GTC GAG GGC CCC AGC AAG GCT GAG ATC TCT TTT GAG GAC CGC AAG GAC        7041
Val Glu Gly Pro Ser Lys Ala Glu Ile Ser Phe Glu Asp Arg Lys Asp
2275                2280                2285                2290

GGC TCC TGT GGT GTG GCT TAT GTG GTC CAG GAG CCA GGT GAC TAC GAA        7089
Gly Ser Cys Gly Val Ala Tyr Val Val Gln Glu Pro Gly Asp Tyr Glu
                2295                2300                2305

GTC TCA GTC AAG TTC AAC GAG GAA CAC ATT CCC GAC AGC CCC TTC GTG        7137
Val Ser Val Lys Phe Asn Glu Glu His Ile Pro Asp Ser Pro Phe Val
        2310                2315                2320

GTG CCT GTG GCT TCT CCG TCT GGC GAC GCC CGC CGC CTC ACT GTT TCT        7185
Val Pro Val Ala Ser Pro Ser Gly Asp Ala Arg Arg Leu Thr Val Ser
        2325                2330                2335

AGC CTT CAG GAG TCA GGG CTA AAG GTC AAC CAG CCA GCC TCT TTT GCA        7233
Ser Leu Gln Glu Ser Gly Leu Lys Val Asn Gln Pro Ala Ser Phe Ala
        2340                2345                2350

GTC AGC CTG AAC GGG GCC AAG GGG GCG ATC GAT GCC AAG GTG CAC AGC        7281
Val Ser Leu Asn Gly Ala Lys Gly Ala Ile Asp Ala Lys Val His Ser
2355                2360                2365                2370

CCC TCA GGA GCC CTG GAG GAG TGC TAT GTC ACA GAA ATT GAC CAA GAT        7329
Pro Ser Gly Ala Leu Glu Glu Cys Tyr Val Thr Glu Ile Asp Gln Asp
                2375                2380                2385

AAG TAT GCT GTG CGC TTC ATC CCT CGG GAG AAT GGC GTT TAC CTG ATT        7377
Lys Tyr Ala Val Arg Phe Ile Pro Arg Glu Asn Gly Val Tyr Leu Ile
        2390                2395                2400

GAC GTC AAG TTC AAC GGT ACC CAC ATC CCT GGA AGC CCC TTC AAG ATC        7425
Asp Val Lys Phe Asn Gly Thr His Ile Pro Gly Ser Pro Phe Lys Ile
        2405                2410                2415

CGA GTT GGG GAG CCT GGG CAT GGA GGG GAC CCA GGC TTG GTG TCT GCT        7473
Arg Val Gly Glu Pro Gly His Gly Gly Asp Pro Gly Leu Val Ser Ala
        2420                2425                2430

TAC GGA GCA GGT CTG GAA GGC GGT GTC ACA GGG AAC CCA GCT GAG TTC        7521
Tyr Gly Ala Gly Leu Glu Gly Gly Val Thr Gly Asn Pro Ala Glu Phe
2435                2440                2445                2450

GTC GTG AAC ACG AGC AAT GCG GGA GCT GGT GCC CTG TCG GTG ACC ATT        7569
Val Val Asn Thr Ser Asn Ala Gly Ala Gly Ala Leu Ser Val Thr Ile
                2455                2460                2465

GAC GGC CCC TCC AAG GTG AAG ATG GAT TGC CAG GAG TGC CCT GAG GGC        7617
Asp Gly Pro Ser Lys Val Lys Met Asp Cys Gln Glu Cys Pro Glu Gly
        2470                2475                2480
```

| | |
|---|---|
| TAC CGC GTC ACC TAT ACC CCC ATG GCA CCT GGC AGC TAC CTC ATC TCC<br>Tyr Arg Val Thr Tyr Thr Pro Met Ala Pro Gly Ser Tyr Leu Ile Ser<br>              2485                            2490                            2495 | 7665 |
| ATC AAG TAC GGC GGC CCC TAC CAC ATT GGG GGC AGC CCC TTC AAG GCC<br>Ile Lys Tyr Gly Gly Pro Tyr His Ile Gly Gly Ser Pro Phe Lys Ala<br>2500                            2505                            2510 | 7713 |
| AAA GTC ACA GGC CCC CGT CTC GTC AGC AAC CAC AGC CTC CAC GAG ACA<br>Lys Val Thr Gly Pro Arg Leu Val Ser Asn His Ser Leu His Glu Thr<br>2515                        2520                        2525                        2530 | 7761 |
| TCA TCA GTG TTT GTA GAC TCT CTG ACC AAG GCC ACC TGT GCC CCC CAG<br>Ser Ser Val Phe Val Asp Ser Leu Thr Lys Ala Thr Cys Ala Pro Gln<br>              2535                            2540                            2545 | 7809 |
| CAT GGG GCC CCG GGT CCT GGG CCT GCT GAC GCC AGC AAG GTG GTG GCC<br>His Gly Ala Pro Gly Pro Gly Pro Ala Asp Ala Ser Lys Val Val Ala<br>                      2550                        2555                        2560 | 7857 |
| AAG GGC CTG GGG CTG AGC AAG GCC TAC GTA GGC CAG AAG AGC AGC TTC<br>Lys Gly Leu Gly Leu Ser Lys Ala Tyr Val Gly Gln Lys Ser Ser Phe<br>2565                        2570                        2575 | 7905 |
| ACA GTA GAC TGC AGC AAA GCA GGC AAC AAC ATG CTG CTG GTG GGG GTT<br>Thr Val Asp Cys Ser Lys Ala Gly Asn Asn Met Leu Leu Val Gly Val<br>              2580                            2585                        2590 | 7953 |
| CAT GGC CCA AGG ACC CCC TGC GAG GAG ATC CTG GTG AAG CAC GTG GGC<br>His Gly Pro Arg Thr Pro Cys Glu Glu Ile Leu Val Lys His Val Gly<br>2595                        2600                        2605                        2610 | 8001 |
| AGC CGG CTC TAC AGC GTG TCC TAC CTG CTC AAG GAC AAG GGG GAG TAC<br>Ser Arg Leu Tyr Ser Val Ser Tyr Leu Leu Lys Asp Lys Gly Glu Tyr<br>                      2615                        2620                        2625 | 8049 |
| ACA CTG GTG GTC AAA TGG GGG CAC GAG CAC ATC CCA GGC AGC CCC TAC<br>Thr Leu Val Val Lys Trp Gly His Glu His Ile Pro Gly Ser Pro Tyr<br>                      2630                        2635                        2640 | 8097 |
| CGC GTT GTG GTG CCC TGAGTCTGGG GCCCGTGCCA GCCGGCAGCC CCCAAGCCTG<br>Arg Val Val Val Pro<br>              2645 | 8152 |
| CCCCGCTACC CAAGCAGCCC CGCCCTCTTC CCCTCAACCC CGGCCCAGGC CGCCCTGGCC | 8212 |
| GCCCGCCTGT CACTGCAGCT GCCCCTGCCC TGTGCCGTGC TGCGCTCACC TGCCTCCCCA | 8272 |
| GCCAGCCGCT GACCTCTCGG CTTTCACTTG GGCAGAGGGA GCCATTTGGT GGCGCTGCTT | 8332 |
| GTCTTCTTTG GTTCTGGGAG GGGTGAGGGA TGGGG | 8367 |

(2) INFORMATION FOR SEQ ID NO:8:

(i) SEQUENCE CHARACTERISTICS:
        (A) LENGTH: 2647 amino acids
        (B) TYPE: amino acid
        (D) TOPOLOGY: Not Relevant (ii) MOLECULE TYPE: protein (xi) SEQUENCE DESCRIPTION: SEQ ID NO:8:

Met Ser Ser Ser His Ser Arg Ala Gly Gln Ser Ala Ala Gly Ala Ala
1                5                    10                  15

Pro Gly Gly Gly Val Asp Thr Arg Asp Ala Glu Met Pro Ala Thr Glu
                    20                    25                    30

Lys Asp Leu Ala Glu Asp Ala Pro Trp Lys Lys Ile Gln Gln Asn Thr
        35                    40                    45

Phe Thr Arg Trp Cys Asn Glu His Leu Lys Cys Val Ser Lys Arg Ile
        50                    55                    60

Ala Asn Leu Gln Thr Asp Leu Ser Asp Gly Leu Arg Leu Ile Ala Leu
65                    70                    75                    80

Leu Glu Val Leu Ser Gln Lys Lys Met His Arg Lys His Asn Gln Arg

```
                    85                  90                  95
Pro Thr Phe Arg Gln Met Gln Leu Glu Asn Val Ser Val Ala Leu Glu
                100                 105                 110
Phe Leu Asp Arg Glu Ser Ile Lys Leu Val Ser Ile Asp Ser Lys Ala
                115                 120                 125
Ile Val Asp Gly Asn Leu Lys Leu Ile Leu Gly Leu Ile Trp Thr Leu
                130                 135                 140
Ile Leu His Tyr Ser Ile Ser Met Pro Met Trp Asp Glu Glu Asp
145                 150                 155                 160
Glu Glu Ala Lys Lys Gln Thr Pro Lys Gln Arg Leu Leu Gly Trp Ile
                165                 170                 175
Gln Asn Lys Leu Pro Gln Leu Pro Ile Thr Asn Phe Ser Arg Asp Trp
                180                 185                 190
Gln Ser Gly Arg Ala Leu Gly Ala Leu Val Asp Ser Cys Ala Pro Gly
                195                 200                 205
Leu Cys Pro Asp Trp Asp Ser Trp Asp Ala Ser Lys Pro Val Thr Asn
210                 215                 220
Ala Arg Glu Ala Met Gln Gln Ala Asp Asp Trp Leu Gly Ile Pro Gln
225                 230                 235                 240
Val Ile Thr Pro Glu Glu Ile Val Asp Pro Asn Val Asp Glu His Ser
                245                 250                 255
Val Met Thr Tyr Leu Ser Gln Phe Pro Lys Ala Lys Leu Lys Pro Gly
                260                 265                 270
Ala Pro Leu Arg Pro Lys Leu Asn Pro Lys Lys Ala Arg Ala Tyr Gly
                275                 280                 285
Pro Gly Ile Glu Pro Thr Gly Asn Met Val Lys Lys Arg Ala Glu Phe
                290                 295                 300
Thr Val Glu Thr Arg Ser Ala Gly Gln Gly Glu Val Leu Val Tyr Val
305                 310                 315                 320
Glu Asp Pro Ala Gly His Gln Glu Glu Ala Lys Val Thr Ala Asn Asn
                325                 330                 335
Asp Lys Asn Arg Thr Phe Ser Val Trp Tyr Val Pro Glu Val Thr Gly
                340                 345                 350
Thr His Lys Val Thr Val Leu Phe Ala Gly Gln His Ile Ala Lys Ser
                355                 360                 365
Pro Phe Glu Val Tyr Val Asp Lys Ser Gln Gly Asp Ala Ser Lys Val
                370                 375                 380
Thr Ala Gln Gly Pro Gly Leu Glu Pro Ser Gly Asn Ile Ala Asn Lys
385                 390                 395                 400
Thr Thr Tyr Phe Glu Ile Phe Thr Ala Gly Ala Gly Thr Gly Glu Val
                405                 410                 415
Glu Val Val Ile Gln Asp Pro Met Gly Gln Lys Gly Thr Val Glu Pro
                420                 425                 430
Gln Leu Glu Ala Arg Gly Asp Ser Thr Tyr Arg Cys Ser Tyr Gln Pro
                435                 440                 445
Thr Met Glu Gly Val His Thr Val His Val Thr Phe Ala Gly Val Pro
                450                 455                 460
Ile Pro Arg Ser Pro Tyr Thr Val Thr Val Gly Gln Ala Cys Asn Pro
465                 470                 475                 480
Ser Ala Cys Arg Ala Val Gly Arg Gly Leu Gln Pro Lys Gly Val Arg
                485                 490                 495
Val Lys Glu Thr Ala Asp Phe Lys Val Tyr Thr Lys Gly Ala Gly Ser
                500                 505                 510
```

-continued

```
Gly Glu Leu Lys Val Thr Val Lys Gly Pro Lys Gly Glu Arg Val
            515                 520                 525
Lys Gln Lys Asp Leu Gly Asp Gly Val Tyr Gly Phe Glu Tyr Tyr Pro
    530                 535                 540
Met Val Pro Gly Thr Tyr Ile Val Thr Ile Thr Trp Gly Gly Gln Asn
545                 550                 555                 560
Ile Gly Arg Ser Pro Phe Glu Val Lys Val Gly Thr Glu Cys Gly Asn
                565                 570                 575
Gln Lys Val Arg Ala Trp Gly Pro Gly Leu Glu Gly Gly Val Val Gly
            580                 585                 590
Lys Ser Ala Asp Phe Val Val Glu Ala Ile Gly Asp Asp Val Gly Thr
    595                 600                 605
Leu Gly Phe Ser Val Glu Gly Pro Ser Gln Ala Lys Ile Glu Cys Asp
    610                 615                 620
Asp Lys Gly Asp Gly Ser Cys Asp Val Arg Tyr Trp Pro Gln Glu Ala
625                 630                 635                 640
Gly Glu Tyr Ala Val His Val Leu Cys Asn Ser Glu Asp Ile Arg Leu
                645                 650                 655
Ser Pro Phe Met Ala Asp Ile Arg Asp Ala Pro Gln Asp Phe His Pro
            660                 665                 670
Asp Arg Val Lys Ala Arg Gly Pro Gly Leu Glu Lys Thr Gly Val Ala
    675                 680                 685
Val Asn Lys Pro Ala Glu Phe Thr Val Asp Ala Lys His Gly Gly Lys
690                 695                 700
Ala Pro Leu Arg Val Gln Val Gln Asp Asn Glu Gly Cys Pro Val Glu
705                 710                 715                 720
Ala Leu Val Lys Asp Asn Gly Asn Gly Thr Tyr Ser Cys Ser Tyr Val
                725                 730                 735
Pro Arg Lys Pro Val Lys His Thr Ala Met Val Ser Trp Gly Gly Val
            740                 745                 750
Ser Ile Pro Asn Ser Pro Phe Arg Val Asn Val Gly Ala Gly Ser His
    755                 760                 765
Pro Asn Lys Val Lys Val Tyr Gly Pro Gly Val Ala Lys Thr Gly Leu
    770                 775                 780
Lys Ala His Glu Pro Thr Tyr Phe Thr Val Asp Cys Ala Glu Ala Gly
785                 790                 795                 800
Gln Gly Asp Val Ser Ile Gly Ile Lys Cys Ala Pro Gly Val Val Gly
                805                 810                 815
Pro Ala Glu Ala Asp Ile Asp Phe Asp Ile Ile Arg Asn Asp Asn Asp
            820                 825                 830
Thr Phe Thr Val Lys Tyr Thr Pro Arg Gly Ala Gly Ser Tyr Thr Ile
    835                 840                 845
Met Val Leu Phe Ala Asp Gln Ala Thr Pro Thr Ser Pro Ile Arg Val
850                 855                 860
Lys Val Glu Pro Ser His Asp Ala Ser Lys Val Lys Ala Glu Gly Pro
865                 870                 875                 880
Gly Leu Ser Arg Thr Gly Val Glu Leu Gly Lys Pro Thr His Phe Thr
                885                 890                 895
Val Asn Ala Lys Ala Ala Gly Lys Gly Lys Leu Asp Val Gln Phe Ser
            900                 905                 910
Gly Leu Thr Lys Gly Asp Ala Val Arg Asp Val Asp Ile Ile Asp His
    915                 920                 925
His Asp Asn Thr Tyr Thr Val Lys Tyr Thr Pro Val Gln Gln Gly Pro
    930                 935                 940
```

Val Gly Val Asn Val Thr Tyr Gly Gly Asp Pro Ile Pro Lys Ser Pro
945                 950                 955                 960

Phe Ser Val Ala Val Ser Pro Ser Leu Asp Leu Ser Lys Ile Lys Val
            965                 970                 975

Ser Gly Leu Gly Glu Lys Val Asp Val Gly Lys Asp Gln Glu Phe Thr
            980                 985                 990

Val Lys Ser Lys Gly Ala Gly Gly Gln Gly Lys Val Ala Ser Lys Ile
        995                 1000                1005

Val Gly Pro Ser Gly Ala Ala Val Pro Cys Lys Val Glu Pro Gly Leu
    1010                1015                1020

Gly Ala Asp Asn Ser Val Val Arg Phe Leu Pro Arg Glu Gly Pro
1025                1030                1035                1040

Tyr Glu Val Glu Val Thr Tyr Asp Gly Val Pro Val Pro Gly Ser Pro
                1045                1050                1055

Phe Pro Leu Glu Ala Val Ala Pro Thr Lys Pro Ser Lys Val Lys Ala
            1060                1065                1070

Phe Gly Pro Gly Leu Gln Gly Gly Ser Ala Gly Ser Pro Ala Arg Phe
        1075                1080                1085

Thr Ile Asp Thr Lys Gly Ala Gly Thr Gly Gly Leu Gly Leu Thr Val
    1090                1095                1100

Glu Gly Pro Cys Glu Ala Gln Leu Glu Cys Leu Asp Asn Gly Asp Gly
1105                1110                1115                1120

Thr Cys Ser Val Ser Tyr Val Pro Thr Glu Pro Gly Asp Tyr Asn Ile
                1125                1130                1135

Asn Ile Leu Phe Ala Asp Thr His Ile Pro Gly Ser Pro Phe Lys Ala
            1140                1145                1150

His Val Val Pro Cys Phe Asp Ala Ser Lys Val Lys Cys Ser Gly Pro
        1155                1160                1165

Gly Leu Glu Arg Ala Thr Ala Gly Glu Val Gly Gln Phe Gln Val Asp
    1170                1175                1180

Cys Ser Ser Ala Gly Ser Ala Glu Leu Thr Ile Glu Ile Cys Ser Glu
1185                1190                1195                1200

Ala Gly Leu Pro Ala Glu Val Tyr Ile Gln Asp His Gly Asp Gly Thr
                1205                1210                1215

His Thr Ile Thr Tyr Ile Pro Leu Cys Pro Gly Ala Tyr Thr Val Thr
            1220                1225                1230

Ile Lys Tyr Gly Gly Gln Pro Val Pro Asn Phe Pro Ser Lys Leu Gln
        1235                1240                1245

Val Glu Pro Ala Val Asp Thr Ser Gly Val Gln Cys Tyr Gly Pro Gly
    1250                1255                1260

Ile Glu Gly Gln Gly Val Phe Arg Glu Ala Thr Thr Glu Phe Ser Val
1265                1270                1275                1280

Asp Ala Arg Ala Leu Thr Gln Thr Gly Gly Pro His Val Lys Ala Arg
                1285                1290                1295

Val Ala Asn Pro Ser Gly Asn Leu Thr Glu Thr Tyr Val Gln Asp Arg
            1300                1305                1310

Gly Asp Gly Met Tyr Lys Val Glu Tyr Thr Pro Tyr Glu Glu Gly Leu
        1315                1320                1325

His Ser Val Asp Val Thr Tyr Asp Gly Ser Pro Val Pro Ser Ser Pro
    1330                1335                1340

Phe Gln Val Pro Val Thr Glu Gly Cys Asp Pro Ser Arg Val Arg Val
1345                1350                1355                1360

His Gly Pro Gly Ile Gln Ser Gly Thr Thr Asn Lys Pro Asn Lys Phe

-continued

```
                1365                1370                1375
Thr Val Glu Thr Arg Gly Ala Gly Thr Gly Gly Leu Gly Leu Ala Val
            1380                1385                1390
Glu Gly Pro Ser Glu Ala Lys Met Ser Cys Met Asp Asn Lys Asp Gly
            1395                1400                1405
Ser Cys Ser Val Glu Tyr Ile Pro Tyr Glu Ala Gly Thr Tyr Ser Leu
            1410                1415                1420
Asn Val Thr Tyr Gly Gly His Gln Val Pro Gly Ser Pro Phe Lys Val
1425                1430                1435                1440
Pro Val His Asp Val Thr Asp Ala Ser Lys Val Lys Cys Ser Gly Pro
            1445                1450                1455
Gly Leu Ser Pro Gly Met Val Arg Ala Asn Leu Pro Gln Ser Phe Gln
            1460                1465                1470
Val Asp Thr Ser Lys Ala Gly Val Ala Pro Leu Gln Val Lys Val Gln
            1475                1480                1485
Gly Pro Lys Gly Leu Val Glu Pro Val Asp Val Val Asp Asn Ala Asp
            1490                1495                1500
Gly Thr Gln Thr Val Asn Tyr Val Pro Ser Arg Glu Gly Pro Tyr Ser
1505                1510                1515                1520
Ile Ser Val Leu Tyr Gly Asp Glu Glu Val Pro Arg Ser Pro Phe Lys
            1525                1530                1535
Val Lys Val Leu Pro Thr His Asp Ala Ser Lys Val Lys Ala Ser Gly
            1540                1545                1550
Pro Gly Leu Asn Thr Thr Gly Val Pro Ala Ser Leu Pro Val Glu Phe
            1555                1560                1565
Thr Ile Asp Ala Lys Asp Ala Gly Glu Gly Leu Leu Ala Val Gln Ile
            1570                1575                1580
Thr Asp Pro Glu Gly Lys Pro Lys Lys Thr His Ile Gln Asp Asn His
1585                1590                1595                1600
Asp Gly Thr Tyr Thr Val Ala Tyr Val Pro Asp Val Thr Gly Arg Tyr
            1605                1610                1615
Thr Ile Leu Ile Lys Tyr Gly Gly Asp Glu Ile Pro Phe Ser Pro Tyr
            1620                1625                1630
Arg Val Arg Ala Val Pro Thr Gly Asp Ala Ser Lys Cys Thr Val Thr
            1635                1640                1645
Val Ser Ile Gly Gly His Gly Leu Gly Ala Gly Ile Gly Pro Thr Ile
            1650                1655                1660
Gln Ile Gly Glu Glu Thr Val Ile Thr Val Asp Thr Lys Ala Ala Gly
1665                1670                1675                1680
Lys Gly Lys Val Thr Cys Thr Val Cys Thr Pro Asp Gly Ser Glu Val
            1685                1690                1695
Asp Val Asp Val Val Glu Asn Glu Asp Gly Thr Phe Asp Ile Phe Tyr
            1700                1705                1710
Thr Ala Pro Gln Pro Gly Lys Tyr Val Ile Cys Val Arg Phe Gly Gly
            1715                1720                1725
Glu His Val Pro Asn Ser Pro Phe Gln Val Thr Ala Leu Ala Gly Asp
            1730                1735                1740
Gln Pro Ser Val Gln Pro Pro Leu Arg Ser Gln Gln Leu Ala Pro Gln
1745                1750                1755                1760
Tyr Thr Tyr Ala Gln Gly Gly Gln Gln Thr Trp Ala Pro Glu Arg Pro
            1765                1770                1775
Leu Val Gly Val Asn Gly Leu Asp Val Thr Ser Leu Arg Pro Phe Asp
            1780                1785                1790
```

-continued

Leu Val Ile Pro Phe Thr Ile Lys Lys Gly Glu Ile Thr Gly Glu Val
    1795                1800                1805

Arg Met Pro Ser Gly Lys Val Ala Gln Pro Thr Ile Thr Asp Asn Lys
    1810                1815                1820

Asp Gly Thr Val Thr Val Arg Tyr Ala Pro Ser Glu Ala Gly Leu His
1825                1830                1835                1840

Glu Met Asp Ile Arg Tyr Asp Asn Met His Ile Pro Gly Ser Pro Leu
                1845                1850                1855

Gln Phe Tyr Val Asp Tyr Val Asn Cys Gly His Val Thr Ala Tyr Gly
                1860                1865                1870

Pro Gly Leu Thr His Gly Val Val Asn Lys Pro Ala Thr Phe Thr Val
                1875                1880                1885

Asn Thr Lys Asp Ala Gly Glu Gly Gly Leu Ser Leu Ala Ile Glu Gly
                1890                1895                1900

Pro Ser Lys Ala Glu Ile Ser Cys Thr Asp Asn Gln Asp Gly Thr Cys
1905                1910                1915                1920

Ser Val Ser Tyr Leu Pro Val Leu Pro Gly Asp Tyr Ser Ile Leu Val
                1925                1930                1935

Lys Tyr Asn Glu Gln His Val Pro Gly Ser Pro Phe Thr Ala Arg Val
                1940                1945                1950

Thr Gly Asp Asp Ser Met Arg Met Ser His Leu Lys Val Gly Ser Ala
                1955                1960                1965

Ala Asp Ile Pro Ile Asn Ile Ser Glu Thr Asp Leu Ser Leu Leu Thr
    1970                1975                1980

Ala Thr Val Val Pro Pro Ser Gly Arg Glu Glu Pro Cys Leu Leu Lys
    1985                1990                1995                2000

Arg Leu Arg Asn Gly His Val Gly Ile Ser Phe Val Pro Lys Glu Thr
                2005                2010                2015

Gly Glu His Leu Val His Val Lys Lys Asn Gly Gln His Val Ala Ser
                2020                2025                2030

Ser Pro Ile Pro Val Val Ile Ser Gln Ser Glu Ile Gly Asp Ala Ser
    2035                2040                2045

Arg Val Arg Val Ser Gly Gln Gly Leu His Glu Gly His Thr Phe Glu
    2050                2055                2060

Pro Ala Glu Phe Ile Ile Asp Thr Arg Asp Ala Gly Tyr Gly Gly Leu
2065                2070                2075                2080

Ser Leu Ser Ile Glu Gly Pro Ser Lys Val Asp Ile Asn Thr Glu Asp
                2085                2090                2095

Leu Glu Asp Gly Thr Cys Arg Val Thr Tyr Cys Pro Thr Glu Pro Gly
                2100                2105                2110

Asn Tyr Ile Ile Asn Ile Lys Phe Ala Asp Gln His Val Pro Gly Ser
                2115                2120                2125

Pro Phe Ser Val Lys Val Thr Gly Glu Gly Arg Val Lys Glu Ser Ile
    2130                2135                2140

Thr Arg Arg Arg Arg Ala Pro Ser Val Ala Asn Val Gly Ser His Cys
2145                2150                2155                2160

Asp Leu Ser Leu Lys Ile Pro Glu Ile Ser Ile Gln Asp Met Thr Ala
                2165                2170                2175

Gln Val Thr Ser Pro Ser Gly Lys Thr His Glu Ala Glu Ile Val Glu
                2180                2185                2190

Gly Glu Asn His Thr Tyr Cys Ile Arg Phe Val Pro Ala Glu Met Gly
                2195                2200                2205

Thr His Thr Val Ser Val Lys Tyr Lys Gly Gln His Val Pro Gly Ser
                2210                2215                2220

```
Pro Phe Gln Phe Thr Val Gly Pro Leu Gly Glu Gly Gly Ala His Lys
2225                2230                2235                2240

Val Arg Ala Gly Gly Pro Gly Leu Glu Arg Ala Glu Ala Gly Val Pro
            2245                2250                2255

Ala Glu Phe Ser Ile Trp Thr Arg Glu Ala Gly Ala Gly Gly Leu Ala
            2260                2265                2270

Ile Ala Val Glu Gly Pro Ser Lys Ala Glu Ile Ser Phe Glu Asp Arg
        2275                2280                2285

Lys Asp Gly Ser Cys Gly Val Ala Tyr Val Val Gln Glu Pro Gly Asp
        2290                2295                2300

Tyr Glu Val Ser Val Lys Phe Asn Glu Glu His Ile Pro Asp Ser Pro
2305                2310                2315                2320

Phe Val Val Pro Val Ala Ser Pro Ser Gly Asp Ala Arg Arg Leu Thr
            2325                2330                2335

Val Ser Ser Leu Gln Glu Ser Gly Leu Lys Val Asn Gln Pro Ala Ser
            2340                2345                2350

Phe Ala Val Ser Leu Asn Gly Ala Lys Gly Ala Ile Asp Ala Lys Val
            2355                2360                2365

His Ser Pro Ser Gly Ala Leu Glu Glu Cys Tyr Val Thr Glu Ile Asp
            2370                2375                2380

Gln Asp Lys Tyr Ala Val Arg Phe Ile Pro Arg Glu Asn Gly Val Tyr
2385                2390                2395                2400

Leu Ile Asp Val Lys Phe Asn Gly Thr His Ile Pro Gly Ser Pro Phe
            2405                2410                2415

Lys Ile Arg Val Gly Glu Pro Gly His Gly Gly Asp Pro Gly Leu Val
            2420                2425                2430

Ser Ala Tyr Gly Ala Gly Leu Glu Gly Gly Val Thr Gly Asn Pro Ala
            2435                2440                2445

Glu Phe Val Val Asn Thr Ser Asn Ala Gly Ala Gly Ala Leu Ser Val
            2450                2455                2460

Thr Ile Asp Gly Pro Ser Lys Val Lys Met Asp Cys Gln Glu Cys Pro
2465                2470                2475                2480

Glu Gly Tyr Arg Val Thr Tyr Thr Pro Met Ala Pro Gly Ser Tyr Leu
            2485                2490                2495

Ile Ser Ile Lys Tyr Gly Gly Pro Tyr His Ile Gly Gly Ser Pro Phe
            2500                2505                2510

Lys Ala Lys Val Thr Gly Pro Arg Leu Val Ser Asn His Ser Leu His
            2515                2520                2525

Glu Thr Ser Ser Val Phe Val Asp Ser Leu Thr Lys Ala Thr Cys Ala
            2530                2535                2540

Pro Gln His Gly Ala Pro Gly Pro Gly Pro Ala Asp Ala Ser Lys Val
2545                2550                2555                2560

Val Ala Lys Gly Leu Gly Leu Ser Lys Ala Tyr Val Gly Gln Lys Ser
            2565                2570                2575

Ser Phe Thr Val Asp Cys Ser Lys Ala Gly Asn Asn Met Leu Leu Val
            2580                2585                2590

Gly Val His Gly Pro Arg Thr Pro Cys Glu Glu Ile Leu Val Lys His
            2595                2600                2605

Val Gly Ser Arg Leu Tyr Ser Val Ser Tyr Leu Leu Lys Asp Lys Gly
            2610                2615                2620

Glu Tyr Thr Leu Val Val Lys Trp Gly His Glu His Ile Pro Gly Ser
2625                2630                2635                2640

Pro Tyr Arg Val Val Val Pro
```

(2) INFORMATION FOR SEQ ID NO:9:

(i) SEQUENCE CHARACTERISTICS:
        (A) LENGTH: 1125 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1125

(xi) SEQUENCE DESCRIPTION: SEQ ID NO:9:

```
TTC GAG ATG TCT GAC TTC ATC GTG GAC ACA AGG GAT GCA GGT TAT GGT       48
Phe Glu Met Ser Asp Phe Ile Val Asp Thr Arg Asp Ala Gly Tyr Gly
 1               5                  10                  15

GGC ATA TCC TTG GCG GTG GAA GGC CCC AGC AAA GTG GAC ATC CAG ACG       96
Gly Ile Ser Leu Ala Val Glu Gly Pro Ser Lys Val Asp Ile Gln Thr
            20                  25                  30

GAG GAC CTG GAA GAT GGC ACC TGC AAA GTC TCC TAC TTC CCT ACC GTG      144
Glu Asp Leu Glu Asp Gly Thr Cys Lys Val Ser Tyr Phe Pro Thr Val
        35                  40                  45

CCT GGG GTT TAT ATC GTC TCC ACC AAA TTC GCT GAC GAG CAC GTG CCT      192
Pro Gly Val Tyr Ile Val Ser Thr Lys Phe Ala Asp Glu His Val Pro
    50                  55                  60

GGG AGC CCA TTT ACC GTG AAG ATC AGT GGG GAG GGA AGA GTC AAA GAG      240
Gly Ser Pro Phe Thr Val Lys Ile Ser Gly Glu Gly Arg Val Lys Glu
 65                  70                  75                  80

AGC ATC ACC CGC ACC AGT CGG GCC CCG TCC GTG GCC ACT GTC GGG AGC      288
Ser Ile Thr Arg Thr Ser Arg Ala Pro Ser Val Ala Thr Val Gly Ser
                 85                  90                  95

ATT TGT GAC CTG AAC CTC AAA ATC CCA GAA ATC AAC AGC AGT GAT ATG      336
Ile Cys Asp Leu Asn Leu Lys Ile Pro Glu Ile Asn Ser Ser Asp Met
            100                 105                 110

TCG GCC CAC GTC ACC AGC CCC TCT GGC CGT GTG ACT GAG GCA GAG ATT      384
Ser Ala His Val Thr Ser Pro Ser Gly Arg Val Thr Glu Ala Glu Ile
        115                 120                 125

GTG CCC ATG GGG AAG AAC TCA CAC TGC GTC CGG TTT GTG CCC CAG GAG      432
Val Pro Met Gly Lys Asn Ser His Cys Val Arg Phe Val Pro Gln Glu
    130                 135                 140

ATG GGC GTG CAC ACG GTC AGC GTC AAG TAC CGT GGG CAG CAC GTC ACC      480
Met Gly Val His Thr Val Ser Val Lys Tyr Arg Gly Gln His Val Thr
145                 150                 155                 160

GGC AGC CCC TTC CAG TTC ACC GTG GGG GCA CTT GGT GAA GGA GGC GCC      528
Gly Ser Pro Phe Gln Phe Thr Val Gly Ala Leu Gly Glu Gly Gly Ala
                165                 170                 175

CAC AAG GTG CGG GCA GGA GGC CCT GGC CTG GAG AGA GGA GAA GCG GGA      576
His Lys Val Arg Ala Gly Gly Pro Gly Leu Glu Arg Gly Glu Ala Gly
            180                 185                 190

GTC CCA GCT GAG TTC AGC ATT TGG ACC CGG GAA GCA GGC GCT GGA GGC      624
Val Pro Ala Glu Phe Ser Ile Trp Thr Arg Glu Ala Gly Ala Gly Gly
        195                 200                 205

CTC TCC ATC GCT GTT GAG GGC CCC AGT AAG GCC GAG ATT ACA TTC GAT      672
Leu Ser Ile Ala Val Glu Gly Pro Ser Lys Ala Glu Ile Thr Phe Asp
    210                 215                 220

GAC CAT AAA AAT GGG TCG TGC GGT GTA TCT TAT ATT GCC CAA GAG CCT      720
Asp His Lys Asn Gly Ser Cys Gly Val Ser Tyr Ile Ala Gln Glu Pro
225                 230                 235                 240

GGT AAC TAC GAG GTG TCC ATC AAG TTC AAT GAT GAG CAC ATC CCG GAA      768
```

```
Gly Asn Tyr Glu Val Ser Ile Lys Phe Asn Asp Glu His Ile Pro Glu
                245                 250                 255

AGC CCC TAC CTG GTG CCG GTC ATC GCA CCC TCC GAC GAC GCC CGC CGC       816
Ser Pro Tyr Leu Val Pro Val Ile Ala Pro Ser Asp Asp Ala Arg Arg
                260                 265                 270

CTC ACT GTT ATG AGC CTT CAG GAA TCG GGA TTA AAA GTT AAC CAG CCA       864
Leu Thr Val Met Ser Leu Gln Glu Ser Gly Leu Lys Val Asn Gln Pro
            275                 280                 285

GCA TCC TTT GCT ATA AGG TTG AAT GGC GCA AAA GGC AAG ATT GAT GCA       912
Ala Ser Phe Ala Ile Arg Leu Asn Gly Ala Lys Gly Lys Ile Asp Ala
        290                 295                 300

AAG GTG CAC AGC CCC TCT GGA GCC GTG GAG GAG TGC CAC GTG TCT GAG       960
Lys Val His Ser Pro Ser Gly Ala Val Glu Glu Cys His Val Ser Glu
305                 310                 315                 320

CTG GAG CCA GAT AAG TAT GCT GTT CGC TTC ATC CCT CAT GAG AAT GGT      1008
Leu Glu Pro Asp Lys Tyr Ala Val Arg Phe Ile Pro His Glu Asn Gly
                325                 330                 335

GTC CAC ACC ATC GAT GTC AAG TTC AAT GGG AGC CAC GTG GTT GGA AGC      1056
Val His Thr Ile Asp Val Lys Phe Asn Gly Ser His Val Val Gly Ser
                340                 345                 350

CCC TTC AAA GTG CGC GTT GGG GAG CCT GGA CAA GCG GGG AAC CCT GCC      1104
Pro Phe Lys Val Arg Val Gly Glu Pro Gly Gln Ala Gly Asn Pro Ala
            355                 360                 365

CTG GTG TCC GCC TAT GGC ACG                                          1125
Leu Val Ser Ala Tyr Gly Thr
        370                 375

(2) INFORMATION FOR SEQ ID NO:10:

(i) SEQUENCE CHARACTERISTICS:
        (A) LENGTH: 375 amino acids
        (B) TYPE: amino acid
        (D) TOPOLOGY: Not Relevant (ii) MOLECULE TYPE: protein (xi) SEQUENCE DESCRIPTION: SEQ ID NO:10:

Phe Glu Met Ser Asp Phe Ile Val Asp Thr Arg Asp Ala Gly Tyr Gly
1               5                   10                  15

Gly Ile Ser Leu Ala Val Glu Gly Pro Ser Lys Val Asp Ile Gln Thr
                20                  25                  30

Glu Asp Leu Glu Asp Gly Thr Cys Lys Val Ser Tyr Phe Pro Thr Val
            35                  40                  45

Pro Gly Val Tyr Ile Val Ser Thr Lys Phe Ala Asp Glu His Val Pro
        50                  55                  60

Gly Ser Pro Phe Thr Val Lys Ile Ser Gly Glu Gly Arg Val Lys Glu
65                  70                  75                  80

Ser Ile Thr Arg Thr Ser Arg Ala Pro Ser Val Ala Thr Val Gly Ser
                85                  90                  95

Ile Cys Asp Leu Asn Leu Lys Ile Pro Glu Ile Asn Ser Ser Asp Met
                100                 105                 110

Ser Ala His Val Thr Ser Pro Ser Gly Arg Val Thr Glu Ala Glu Ile
            115                 120                 125

Val Pro Met Gly Lys Asn Ser His Cys Val Arg Phe Val Pro Gln Glu
        130                 135                 140

Met Gly Val His Thr Val Ser Val Lys Tyr Arg Gly Gln His Val Thr
145                 150                 155                 160

Gly Ser Pro Phe Gln Phe Thr Val Gly Ala Leu Gly Glu Gly Gly Ala
                165                 170                 175
```

```
His Lys Val Arg Ala Gly Gly Pro Gly Leu Glu Arg Gly Glu Ala Gly
            180                 185                 190

Val Pro Ala Glu Phe Ser Ile Trp Thr Arg Glu Ala Gly Ala Gly Gly
            195                 200                 205

Leu Ser Ile Ala Val Glu Gly Pro Ser Lys Ala Glu Ile Thr Phe Asp
210                 215                 220

Asp His Lys Asn Gly Ser Cys Gly Val Ser Tyr Ile Ala Gln Glu Pro
225                 230                 235                 240

Gly Asn Tyr Glu Val Ser Ile Lys Phe Asn Asp Glu His Ile Pro Glu
                245                 250                 255

Ser Pro Tyr Leu Val Pro Val Ile Ala Pro Ser Asp Asp Ala Arg Arg
            260                 265                 270

Leu Thr Val Met Ser Leu Gln Glu Ser Gly Leu Lys Val Asn Gln Pro
            275                 280                 285

Ala Ser Phe Ala Ile Arg Leu Asn Gly Ala Lys Gly Lys Ile Asp Ala
290                 295                 300

Lys Val His Ser Pro Ser Gly Ala Val Glu Glu Cys His Val Ser Glu
305                 310                 315                 320

Leu Glu Pro Asp Lys Tyr Ala Val Arg Phe Ile Pro His Glu Asn Gly
                325                 330                 335

Val His Thr Ile Asp Val Lys Phe Asn Gly Ser His Val Val Gly Ser
            340                 345                 350

Pro Phe Lys Val Arg Val Gly Glu Pro Gly Gln Ala Gly Asn Pro Ala
            355                 360                 365

Leu Val Ser Ala Tyr Gly Thr
370                 375

(2) INFORMATION FOR SEQ ID NO:11:

(i) SEQUENCE CHARACTERISTICS:
        (A) LENGTH: 1494 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1449

(xi) SEQUENCE DESCRIPTION: SEQ ID NO:11:

AAA ATC CCA GAA ATC AAC AGC AGT GAT ATG TCG GCC CAC GTC ACC AGC        48
Lys Ile Pro Glu Ile Asn Ser Ser Asp Met Ser Ala His Val Thr Ser
1               5                   10                  15

CCC TCT GGC CGT GTG ACT GAG GCA GAG ATT GTG CCC ATG GGG AAG AAC        96
Pro Ser Gly Arg Val Thr Glu Ala Glu Ile Val Pro Met Gly Lys Asn
            20                  25                  30

TCA CAC TGC GTC CGG TTT GTG CCC CAG GAG ATG GGC GTG CAC ACG GTC       144
Ser His Cys Val Arg Phe Val Pro Gln Glu Met Gly Val His Thr Val
        35                  40                  45

AGC GTC AAG TAC CGT GGG CAG CAC GTC ACC GGC AGC CCC TTC CAG TTC       192
Ser Val Lys Tyr Arg Gly Gln His Val Thr Gly Ser Pro Phe Gln Phe
    50                  55                  60

ACC GTG GGG GCA CTT GGT GAA GGA GGC GCC CAC AAG GTG CGG GCA GGA       240
Thr Val Gly Ala Leu Gly Glu Gly Gly Ala His Lys Val Arg Ala Gly
65                  70                  75                  80

GGC CCT GGC CTG GAG AGA GGA GAA GCG GGA GTC CCA GCT GAG TTC AGC       288
Gly Pro Gly Leu Glu Arg Gly Glu Ala Gly Val Pro Ala Glu Phe Ser
                85                  90                  95
```

| | | |
|---|---|---|
| ATT TGG ACC CGG GAA GCA GGC GCT GGA GGC CTC TCC ATC GCT GTT GAG<br>Ile Trp Thr Arg Glu Ala Gly Ala Gly Gly Leu Ser Ile Ala Val Glu<br>100              105              110 | | 336 |
| GGC CCC AGT AAG GCC GAG ATT ACA TTC GAT GAC CAT AAA AAT GGG TCG<br>Gly Pro Ser Lys Ala Glu Ile Thr Phe Asp Asp His Lys Asn Gly Ser<br>     115              120              125 | | 384 |
| TGC GGT GTA TCT TAT ATT GCC CAA GAG CCT GGT AAC TAC GAG GTG TCC<br>Cys Gly Val Ser Tyr Ile Ala Gln Glu Pro Gly Asn Tyr Glu Val Ser<br>130              135              140 | | 432 |
| ATC AAG TTC AAT GAT GAG CAC ATC CCG GAA AGC CCC TAC CTG GTG CCG<br>Ile Lys Phe Asn Asp Glu His Ile Pro Glu Ser Pro Tyr Leu Val Pro<br>145              150              155              160 | | 480 |
| GTC ATC GCA CCC TCC GAC GAC GCC CGC CGC CTC ACT GTT ATG AGC CTT<br>Val Ile Ala Pro Ser Asp Asp Ala Arg Arg Leu Thr Val Met Ser Leu<br>              165              170              175 | | 528 |
| CAG GAA TCG GGA TTA AAA GTT AAC CAG CCA GCA TCC TTT GCT ATA AGG<br>Gln Glu Ser Gly Leu Lys Val Asn Gln Pro Ala Ser Phe Ala Ile Arg<br>              180              185              190 | | 576 |
| TTG AAT GGC GCA AAA GGC AAG ATT GAT GCA AAG GTG CAC AGC CCC TCT<br>Leu Asn Gly Ala Lys Gly Lys Ile Asp Ala Lys Val His Ser Pro Ser<br>          195              200              205 | | 624 |
| GGA GCC GTG GAG GAG TGC CAC GTG TCT GAG CTG GAG CCA GAT AAG TAT<br>Gly Ala Val Glu Glu Cys His Val Ser Glu Leu Glu Pro Asp Lys Tyr<br>210              215              220 | | 672 |
| GCT GTT CGC TTC ATC CCT CAT GAG AAT GGT GTC CAC ACC ATC GAT GTC<br>Ala Val Arg Phe Ile Pro His Glu Asn Gly Val His Thr Ile Asp Val<br>225              230              235              240 | | 720 |
| AAG TTC AAT GGG AGC CAC GTG GTT GGA AGC CCC TTC AAA GTG CGC GTT<br>Lys Phe Asn Gly Ser His Val Val Gly Ser Pro Phe Lys Val Arg Val<br>              245              250              255 | | 768 |
| GGG GAG CCT GGA CAA GCG GGG AAC CCT GCC CTG GTG TCC GCC TAT GGC<br>Gly Glu Pro Gly Gln Ala Gly Asn Pro Ala Leu Val Ser Ala Tyr Gly<br>              260              265              270 | | 816 |
| ACG GGA CTC GAA GGG GGN ACC ACA GGT ATC CAG TCG GAA TTC TTT ATT<br>Thr Gly Leu Glu Gly Xaa Thr Thr Gly Ile Gln Ser Glu Phe Phe Ile<br>          275              280              285 | | 864 |
| AAC ACC ACC CGA GCA GGT CCA GGG ACA TTA TCC GTC ACC ATC GAA GGC<br>Asn Thr Thr Arg Ala Gly Pro Gly Thr Leu Ser Val Thr Ile Glu Gly<br>290              295              300 | | 912 |
| CCA TCC AAG GTT AAA ATG GAT TGC CAG GAA ACA CCT GAA GGG TAC AAA<br>Pro Ser Lys Val Lys Met Asp Cys Gln Glu Thr Pro Glu Gly Tyr Lys<br>305              310              315              320 | | 960 |
| GTC ATG TAC ACC CCC ATG GCT CCT GGT AAC TAC CTG ATC AGT GTC AAA<br>Val Met Tyr Thr Pro Met Ala Pro Gly Asn Tyr Leu Ile Ser Val Lys<br>              325              330              335 | | 1008 |
| TAC GGT GGG CCC AAC CAC ATC GTG GGC AGT CCC TTC AAG GCC AAG GTG<br>Tyr Gly Gly Pro Asn His Ile Val Gly Ser Pro Phe Lys Ala Lys Val<br>              340              345              350 | | 1056 |
| ACT GGC CAG CGT CTA GTT AGC CCT GGC TCA GCC AAC GAG ACC TCA TCC<br>Thr Gly Gln Arg Leu Val Ser Pro Gly Ser Ala Asn Glu Thr Ser Ser<br>          355              360              365 | | 1104 |
| ATC CTG GTG GAG TCA GTG ACC AGG TCG TCT ACA GAG ACC TGC TAT AGC<br>Ile Leu Val Glu Ser Val Thr Arg Ser Ser Thr Glu Thr Cys Tyr Ser<br>370              375              380 | | 1152 |
| GCC ATT CCC AAG GCA TCC TCG GAC GCC AGC AAG GTG ACC TCT AAG GGG<br>Ala Ile Pro Lys Ala Ser Ser Asp Ala Ser Lys Val Thr Ser Lys Gly<br>385              390              395              400 | | 1200 |
| GCA GGG CTC TCA AAG GCC TTT GTG GGC CAG AAG AGT TCC TTC CTG GTG<br>Ala Gly Leu Ser Lys Ala Phe Val Gly Gln Lys Ser Ser Phe Leu Val<br>              405              410              415 | | 1248 |

```
GAC TGC AGC AAA GCT GGC TCC AAC ATG CTG CTG ATC GGG GTC CAT GGG         1296
Asp Cys Ser Lys Ala Gly Ser Asn Met Leu Leu Ile Gly Val His Gly
        420                 425                 430

CCC ACC ACC CCC TGC GAG GAG GTC TCC ATG AAG CAT GTA GGC AAC CAG         1344
Pro Thr Thr Pro Cys Glu Glu Val Ser Met Lys His Val Gly Asn Gln
        435                 440                 445

CAA TAC AAC GTC ACA TAC GTC GTC AAG GAG AGG GGC GAT TAT GTG CTG         1392
Gln Tyr Asn Val Thr Tyr Val Val Lys Glu Arg Gly Asp Tyr Val Leu
450                 455                 460

GCT GTG AAG TGG GGG GAG GAA CAC ATC CCT GGC AGC CCT TTT CAT GTC         1440
Ala Val Lys Trp Gly Glu Glu His Ile Pro Gly Ser Pro Phe His Val
465                 470                 475                 480

ACA GTG CCT TAAAACAGTT TTCTCAAATC CTGGAAAAAA AAAAAAAAAA AAAAA           1494
Thr Val Pro
```

(2) INFORMATION FOR SEQ ID NO:12:

(i) SEQUENCE CHARACTERISTICS:
        (A) LENGTH: 483 amino acids
        (B) TYPE: amino acid
        (D) TOPOLOGY: Not Relevant (ii) MOLECULE TYPE: protein (xi) SEQUENCE DESCRIPTION: SEQ ID NO:12:

```
Lys Ile Pro Glu Ile Asn Ser Ser Asp Met Ser Ala His Val Thr Ser
1               5                   10                  15

Pro Ser Gly Arg Val Thr Glu Ala Glu Ile Val Pro Met Gly Lys Asn
            20                  25                  30

Ser His Cys Val Arg Phe Val Pro Gln Glu Met Gly Val His Thr Val
        35                  40                  45

Ser Val Lys Tyr Arg Gly Gln His Val Thr Gly Ser Pro Phe Gln Phe
    50                  55                  60

Thr Val Gly Ala Leu Gly Glu Gly Gly Ala His Lys Val Arg Ala Gly
65                  70                  75                  80

Gly Pro Gly Leu Glu Arg Gly Glu Ala Gly Val Pro Ala Glu Phe Ser
                85                  90                  95

Ile Trp Thr Arg Glu Ala Gly Ala Gly Gly Leu Ser Ile Ala Val Glu
            100                 105                 110

Gly Pro Ser Lys Ala Glu Ile Thr Phe Asp Asp His Lys Asn Gly Ser
        115                 120                 125

Cys Gly Val Ser Tyr Ile Ala Gln Glu Pro Gly Asn Tyr Glu Val Ser
    130                 135                 140

Ile Lys Phe Asn Asp Glu His Ile Pro Glu Ser Pro Tyr Leu Val Pro
145                 150                 155                 160

Val Ile Ala Pro Ser Asp Asp Ala Arg Arg Leu Thr Val Met Ser Leu
                165                 170                 175

Gln Glu Ser Gly Leu Lys Val Asn Gln Pro Ala Ser Phe Ala Ile Arg
            180                 185                 190

Leu Asn Gly Ala Lys Gly Lys Ile Asp Ala Lys Val His Ser Pro Ser
        195                 200                 205

Gly Ala Val Glu Glu Cys His Val Ser Glu Leu Glu Pro Asp Lys Tyr
    210                 215                 220

Ala Val Arg Phe Ile Pro His Glu Asn Gly Val His Thr Ile Asp Val
225                 230                 235                 240

Lys Phe Asn Gly Ser His Val Val Gly Ser Pro Phe Lys Val Arg Val
                245                 250                 255

Gly Glu Pro Gly Gln Ala Gly Asn Pro Ala Leu Val Ser Ala Tyr Gly
```

```
                260                 265                 270
Thr Gly Leu Glu Gly Xaa Thr Thr Gly Ile Gln Ser Glu Phe Phe Ile
            275                 280                 285
Asn Thr Thr Arg Ala Gly Pro Gly Thr Leu Ser Val Thr Ile Glu Gly
290                 295                 300
Pro Ser Lys Val Lys Met Asp Cys Gln Glu Thr Pro Glu Gly Tyr Lys
305                 310                 315                 320
Val Met Tyr Thr Pro Met Ala Pro Gly Asn Tyr Leu Ile Ser Val Lys
                325                 330                 335
Tyr Gly Gly Pro Asn His Ile Val Gly Ser Pro Phe Lys Ala Lys Val
                340                 345                 350
Thr Gly Gln Arg Leu Val Ser Pro Gly Ser Ala Asn Glu Thr Ser Ser
            355                 360                 365
Ile Leu Val Glu Ser Val Thr Arg Ser Ser Thr Glu Thr Cys Tyr Ser
370                 375                 380
Ala Ile Pro Lys Ala Ser Ser Asp Ala Ser Lys Val Thr Ser Lys Gly
385                 390                 395                 400
Ala Gly Leu Ser Lys Ala Phe Val Gly Gln Lys Ser Ser Phe Leu Val
                405                 410                 415
Asp Cys Ser Lys Ala Gly Ser Asn Met Leu Leu Ile Gly Val His Gly
            420                 425                 430
Pro Thr Thr Pro Cys Glu Glu Val Ser Met Lys His Val Gly Asn Gln
            435                 440                 445
Gln Tyr Asn Val Thr Tyr Val Val Lys Glu Arg Gly Asp Tyr Val Leu
            450                 455                 460
Ala Val Lys Trp Gly Glu Glu His Ile Pro Gly Ser Pro Phe His Val
465                 470                 475                 480
Thr Val Pro
```

(2) INFORMATION FOR SEQ ID NO:13:

(i) SEQUENCE CHARACTERISTICS:
        (A) LENGTH: 53 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:13:

```
Tyr Arg Leu Ser Val Glu Ile Tyr Asp Arg Arg Glu Tyr Ser Arg Phe
1               5                   10                  15
Glu Lys Glu Gln Gln Gln Leu Asn Trp Lys Gln Asp Ser Asn Pro Leu
            20                  25                  30
Tyr Lys Ser Ala Ile Thr Thr Thr Ile Asn Pro Arg Phe Gln Glu Ala
        35                  40                  45
Asp Ser Pro Thr Leu
    50
```

(2) INFORMATION FOR SEQ ID NO:14:

(i) SEQUENCE CHARACTERISTICS:
        (A) LENGTH: 31 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:14:

```
Tyr Arg Leu Ser Val Glu Ile Tyr Asp Arg Arg Glu Tyr Ser Arg Phe
1               5                   10                  15

Glu Lys Glu Gln Gln Gln Leu Asn Trp Lys Gln Asp Ser Asn Pro
                20                  25                  30
```

(2) INFORMATION FOR SEQ ID NO:15:

(i) SEQUENCE CHARACTERISTICS:
        (A) LENGTH: 36 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:15:

```
Tyr Arg Leu Ser Val Glu Ile Tyr Asp Arg Arg Glu Tyr Ser Arg Phe
1               5                   10                  15

Glu Lys Glu Gln Gln Gln Leu Asn Trp Lys Gln Asp Ser Asn Pro Leu
                20                  25                  30
Tyr Lys Ser Ala
            35
```

(2) INFORMATION FOR SEQ ID NO:16:

(i) SEQUENCE CHARACTERISTICS:
        (A) LENGTH: 43 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:16:

```
Tyr Arg Leu Ser Val Glu Ile Tyr Asp Arg Arg Glu Tyr Ser Arg Phe
1               5                   10                  15

Glu Lys Glu Gln Gln Gln Leu Asn Trp Lys Gln Asp Ser Asn Pro Leu
                20                  25                  30

Tyr Lys Ser Ala Ile Thr Thr Thr Ile Asn Pro
            35                  40
```

(2) INFORMATION FOR SEQ ID NO:17:

(i) SEQUENCE CHARACTERISTICS:
        (A) LENGTH: 19 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:17:

```
Tyr Arg Leu Ser Val Glu Ile Tyr Asp Arg Arg Glu Tyr Ser Arg Phe
1               5                   10                  15

Glu Lys Glu
```

(2) INFORMATION FOR SEQ ID NO:18:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:18:

```
Tyr Arg Leu Ser Val Glu Ile Tyr Asp Arg Arg Glu Tyr Ser Arg
1               5                   10                  15
```

(2) INFORMATION FOR SEQ ID NO:19:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:19:

GATGGCACTT TTGTACTAAG GATTACTGTC CTG     33

(2) INFORMATION FOR SEQ ID NO:20:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:20:

ATTGATGGTG GTCGTCTAGG CACTTTTGTA GAG     33

(2) INFORMATION FOR SEQ ID NO:21:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:21:

GTCTGCCTCT TGAAACTAAG GATTGATGGT GGT     33

(2) INFORMATION FOR SEQ ID NO:22:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:22:

CCAGTTGAGT TGTTGCTACT CCTTCTCAAA GCG     33

(2) INFORMATION FOR SEQ ID NO:23:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:23:

GTTGCTGCTC CTTCTCCTAG CGACTGTATT CCCG     34

-continued (2) INFORMATION FOR SEQ ID NO:24:

(i) SEQUENCE CHARACTERISTICS:
        (A) LENGTH: 53 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:24:

Tyr Arg Leu Ala Val Glu Ile Tyr Asp Arg Arg Glu Tyr Ser Arg Phe Glu
1            5                  10                15

Lys Glu Gln Gln Gln Leu Asn Trp Lys Gln Asp Ser Asn Pro Leu Tyr
        20                25                30

Lys Ser Ala Ile Thr Thr Thr Ile Asn Pro Arg Phe Gln Glu Ala Asp
   35                 40                45

Ser Pro Thr Leu
50

(2) INFORMATION FOR SEQ ID NO:25:

(i) SEQUENCE CHARACTERISTICS:
        (A) LENGTH: 53 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:25:

Tyr Arg Leu Ser Val Gln Ile Tyr Asp Arg Arg Glu Tyr Ser Arg Phe Glu
1            5                  10                15

Lys Glu Gln Gln Gln Leu Asn Trp Lys Gln Asp Ser Asn Pro Leu Tyr
        20                25                30

Lys Ser Ala Ile Thr Thr Thr Ile Asn Pro Arg Phe Gln Glu Ala Asp
   35                 40                45

Ser Pro Thr Leu
50

(2) INFORMATION FOR SEQ ID NO:26:

(i) SEQUENCE CHARACTERISTICS:
        (A) LENGTH: 53 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:26:

Tyr Arg Leu Ser Val Glu Ile Tyr Asp Ala Arg Glu Tyr Ser Arg Phe Glu
1            5                  10                15

Lys Glu Gln Gln Gln Leu Asn Trp Lys Gln Asp Ser Asn Pro Leu Tyr
        20                25                30

Lys Ser Ala Ile Thr Thr Thr Ile Asn Pro Arg Phe Gln Glu Ala Asp
   35                 40                45

Ser Pro Thr Leu
50

(2) INFORMATION FOR SEQ ID NO:27:

(i) SEQUENCE CHARACTERISTICS:
        (A) LENGTH: 53 amino acids
        (B) TYPE: amino acid (C) STRANDEDNESS: Not Relevant
        (D) TOPOLOGY: Not Relevant (ii) MOLECULE TYPE: peptide (xi) SEQUENCE DESCRIPTION: SEQ ID NO:27:

Tyr Arg Leu Ser Val Glu Ile Tyr Asp Arg Arg Glu Tyr Ala Arg Phe Glu
1               5                   10                  15

Lys Glu Gln Gln Gln Leu Asn Trp Lys Gln Asp Ser Asn Pro Leu Tyr
        20                  25                  30

Lys Ser Ala Ile Thr Thr Thr Ile Asn Pro Arg Phe Gln Glu Ala Asp
        35                  40                  45

Ser Pro Thr Leu
50

(2) INFORMATION FOR SEQ ID NO:28:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:28:

GTCATAGATT TCCACCGCGA GCCGGTATCC GAG                                   33

(2) INFORMATION FOR SEQ ID NO:29:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:29:

CCGGCCGTCA TAGATTTGCA CCGAGAGCCG GTATC                                 35

(2) INFORMATION FOR SEQ ID NO:30:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:30:

GCGACTGTAT TCCCGCGCGT CATAGATTTC CAC                                   33

(2) INFORMATION FOR SEQ ID NO:31:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:31:

CTCCTTCTCA AAGCGCGCGT ATTCCCGGCG GTC                                   33

(2) INFORMATION FOR SEQ ID NO:32:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:32:

ATATCTCGAG AGTATACCCC CATGGCACCT                                               30

(2) INFORMATION FOR SEQ ID NO:33:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucelic acid (xi) SEQUENCE DESCRIPTION: SEQ ID NO:33:

ATATCTCGAG TCAGGGCACC ACAACGCG                                                 28

(2) INFORMATION FOR SEQ ID NO:34:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:34:

ATATCTCGAG TCAGCTGCTC TTCTGGCCCT AC                                       32

(2) INFORMATION FOR SEQ ID NO:35:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:35:

ATATCATATG TACACCCCCA TGGCTCCT                                                 28

(2) INFORMATION FOR SEQ ID NO:36:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:36:

ATAGGATCCT CAGCCCCACA AACAGGC                                                  27

(2) INFORMATION FOR SEQ ID NO:37:

(i) SEQUENCE CHARACTERISTICS:
        (A) LENGTH: 30 base pairs
        (B) TYPE: nucleic acid (C) STRANDEDNESS: single
(D) TOPOLOGY: linear (ii) MOLECULE TYPE: other nucleic acid (xi) SEQUENCE DESCRIPTION: SEQ ID NO:37:

GGTGGCCTTG GTCAGAGAGT CTACAAACAC                              30

(2) INFORMATION FOR SEQ ID NO:38:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: other nucleic acid (xi) SEQUENCE DESCRIPTION: SEQ ID NO:38:

GGCGCTATAG CAGGTCTCTG TAGACGACCT                              30

(2) INFORMATION FOR SEQ ID NO:39:

(i) SEQUENCE CHARACTERISTICS:
       (A) LENGTH: 11 amino acids
       (B) TYPE: amino acid
       (C) STRANDEDNESS: Not Relevant
       (D) TOPOLOGY: Not Relevant (ii) MOLECULE TYPE: peptide (xi) SEQUENCE DESCRIPTION: SEQ ID NO:39:

Tyr Arg Leu Ser Val Glu Ile Tyr Asp Arg Arg
1               5                   10

(2) INFORMATION FOR SEQ ID NO:40:

(i) SEQUENCE CHARACTERISTICS:
       (A) LENGTH: 49 amino acids
       (B) TYPE: amino acid
       (C) STRANDEDNESS: Not Relevant
       (D) TOPOLOGY: Not Relevant (ii) MOLECULE TYPE: peptide (xi) SEQUENCE DESCRIPTION: SEQ ID NO:40:

Tyr Arg Leu Ser Val Glu Ile Tyr Asp Arg Arg Glu Tyr Ser Arg Phe
1               5                   10                  15

Glu Lys Glu Gln Gln Gln Leu Asn Trp Lys Gln Asp Ser Asn Pro Leu
            20                  25                  30

Tyr Lys Ser Ala Ile Thr Thr Thr Ile Asn Pro Arg Phe Gln Glu Ala
        35                  40                  45

Asp (2) INFORMATION FOR SEQ ID NO:41:

(i) SEQUENCE CHARACTERISTICS:
       (A) LENGTH: 45 amino acids
       (B) TYPE: amino acid
       (C) STRANDEDNESS: Not Relevant
       (D) TOPOLOGY: Not Relevant (ii) MOLECULE TYPE: peptide (xi) SEQUENCE DESCRIPTION: SEQ ID NO:41:

Tyr Arg Leu Ser Val Glu Ile Tyr Asp Arg Arg Glu Tyr Ser Arg Phe
1               5                   10                  15

```
Glu Lys Glu Gln Gln Gln Leu Asn Trp Lys Gln Asp Ser Asn Pro Leu
         20                  25                  30

Tyr Lys Ser Ala Ile Thr Thr Thr Ile Asn Pro Arg Phe
         35                  40                  45
```

(2) INFORMATION FOR SEQ ID NO:42:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:42:

CTCAAAGCGA CTGTACTACC GGCGGTCATA GATTTC                        36

(2) INFORMATION FOR SEQ ID NO:43:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:43:

CTTTCAAGAG GCAGACTGAC CCACTCTCTG AGGA                          34

(2) INFORMATION FOR SEQ ID NO:44:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:44:

TCCTCAGAGA GTGGGTCAGT CTGCCTCTTG AAAG                          34

(2) INFORMATION FOR SEQ ID NO:45:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:45:

CATCAATCCT CGCTTTTGAG AGGCAGACAG TCCC                          34

(2) INFORMATION FOR SEQ ID NO:46:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:46:

GGGACTGTCT GCCTCTCAAA AGCGAGGATT GATC                          34

(2) INFORMATION FOR SEQ ID NO:47:

(i) SEQUENCE CHARACTERISTICS:
        (A) LENGTH: 53 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:47:

```
Tyr Arg Leu Ser Phe Glu Ile Tyr Asp Arg Arg Glu Tyr Ser Arg Phe
1               5                   10                  15

Glu Lys Glu Gln Gln Gln Leu Asn Trp Lys Gln Asp Ser Asn Pro Leu
            20                  25                  30

Tyr Lys Ser Ala Ile Thr Thr Thr Ile Asn Pro Arg Phe Gln Glu Ala
            35                  40                  45

Asp Ser Pro Thr Leu
        50
```

(2) INFORMATION FOR SEQ ID NO:48:

(i) SEQUENCE CHARACTERISTICS:
        (A) LENGTH: 53 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:48:

```
Tyr Arg Leu Ser Val Glu Phe Tyr Asp Arg Arg Glu Tyr Ser Arg Phe
1               5                   10                  15

Glu Lys Glu Gln Gln Gln Leu Asn Trp Lys Gln Asp Ser Asn Pro Leu
            20                  25                  30

Tyr Lys Ser Ala Ile Thr Thr Thr Ile Asn Pro Arg Phe Gln Glu Ala
            35                  40                  45

Asp Ser Pro Thr Leu
        50
```

(2) INFORMATION FOR SEQ ID NO:49:

(i) SEQUENCE CHARACTERISTICS:
        (A) LENGTH: 53 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:49:

```
Tyr Arg Leu Ser Val Glu Ile Phe Asp Arg Arg Glu Tyr Ser Arg Phe
1               5                   10                  15

Glu Lys Glu Gln Gln Gln Leu Asn Trp Lys Gln Asp Ser Asn Pro Leu
            20                  25                  30

Tyr Lys Ser Ala Ile Thr Thr Thr Ile Asn Pro Arg Phe Gln Glu Ala
            35                  40                  45

Asp Ser Pro Thr Leu
        50
```

(2) INFORMATION FOR SEQ ID NO:50:

(i) SEQUENCE CHARACTERISTICS:

(A) LENGTH: 53 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:50:

Tyr Arg Leu Ser Val Glu Ile Tyr Ala Arg Arg Glu Tyr Ser Arg Phe
    1               5                  10                  15

Glu Lys Glu Gln Gln Gln Leu Asn Trp Lys Gln Asp Ser Asn Pro Leu
                20                  25                  30

Tyr Lys Ser Ala Ile Thr Thr Thr Ile Asn Pro Arg Phe Gln Glu Ala
                35                  40                  45

Asp Ser Pro Thr Leu
                50

(2) INFORMATION FOR SEQ ID NO:51:

(i) SEQUENCE CHARACTERISTICS:
        (A) LENGTH: 53 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:51:

Tyr Arg Leu Ser Val Glu Ile Tyr Asp Arg Ala Glu Tyr Ser Arg Phe
    1               5                  10                  15

Glu Lys Glu Gln Gln Gln Leu Asn Trp Lys Gln Asp Ser Asn Pro Leu
                20                  25                  30

Tyr Lys Ser Ala Ile Thr Thr Thr Ile Asn Pro Arg Phe Gln Glu Ala
                35                  40                  45

Asp Ser Pro Thr Leu
                50

(2) INFORMATION FOR SEQ ID NO:52:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:52:

GCGGTCATAG ATTTCAAACG AGAGCCGGTA TCC                                33

(2) INFORMATION FOR SEQ ID NO:53:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:53:

TTCCCGGCGG TCATAGAATT CCACCGAGAG CCG                                33

(2) INFORMATION FOR SEQ ID NO:54:

(i) SEQUENCE CHARACTERISTICS:

(A) LENGTH: 33 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:54:

GTATTCCCGG CGGTCAAAGA TTTCCACCGA GAG                                33

(2) INFORMATION FOR SEQ ID NO:55:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:55:

ACTGTATTCC CGGCGCGCAT AGATTTCCAC CGA                                33

(2) INFORMATION FOR SEQ ID NO:56:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:56:

AAAGCGACTG TATTCCGCGC GGTCATAGAT TTC                                33

(2) INFORMATION FOR SEQ ID NO:57:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:57:

CCCGAATTCA CAGGCCCCCG TCTCGTC                                       27

(2) INFORMATION FOR SEQ ID NO:58:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:58:

CCCGAATTCC TCGAGTCAGG GCACCACAAC GCGGTAG                            37

(2) INFORMATION FOR SEQ ID NO:59:

(i) SEQUENCE CHARACTERISTICS:
        (A) LENGTH: 31 base pairs
        (B) TYPE: nucleic acid
        (C) STRANDEDNESS: single
        (D) TOPOLOGY: linear

```
        (ii) MOLECULE TYPE: other nucleic acid (xi) SEQUENCE DESCRIPTION: SEQ ID NO:59:

CCCCCTCGAG GCTACTGCAT CCGCTTTGTT C                                   31

(2) INFORMATION FOR SEQ ID NO:60:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: other nucleic acid (xi) SEQUENCE DESCRIPTION: SEQ ID NO:60:

CCCCTCGAGT CAGTAAGCAG ACACCAAGCC                                     30

(2) INFORMATION FOR SEQ ID NO:61:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: other nucleic acid (xi) SEQUENCE DESCRIPTION: SEQ ID NO:61:

CCCCTCGAGC CAGCCTCTTT TGCAGTC                                        27

(2) INFORMATION FOR SEQ ID NO:62:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: other nucleic acid (xi) SEQUENCE DESCRIPTION: SEQ ID NO:62:

CCCCTCGAGC CAGCCGAATT CAGTATC                                        27

(2) INFORMATION FOR SEQ ID NO:63:

(i) SEQUENCE CHARACTERISTICS:
         (A) LENGTH: 31 base pairs
         (B) TYPE: nucleic acid
         (C) STRANDEDNESS: single
         (D) TOPOLOGY: linear (ii) MOLECULE TYPE: other nucleic acid (xi) SEQUENCE DESCRIPTION: SEQ ID NO:63:

CCCCTCGAGT CACGCCCCCT TGGCCCCCTT C                                   31

(2) INFORMATION FOR SEQ ID NO:64:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: other nucleic acid (xi) SEQUENCE DESCRIPTION: SEQ ID NO:64:

CCCCCTCGAG GCGGCACGGG ACTCGAAGGG                                     30
```

(2) INFORMATION FOR SEQ ID NO:65:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:65:

CCCCTCGAGT TAAGGCACTG TGACATG        27